US011447789B2

(12) United States Patent
Hall et al.

(10) Patent No.: US 11,447,789 B2
(45) Date of Patent: Sep. 20, 2022

(54) PRODUCTION IN PLANTS OF RICIN ANTIBODIES THAT BIND TO RICIN B CHAIN

(71) Applicant: HER MAJESTY THE QUEEN IN RIGHT OF CANADA, AS REPRESENTED BY THE MINISTER OF NATIONAL DEFENCE, Ottawa (CA)

(72) Inventors: J. Christopher Hall, Whistler (CA); Ashley J. Meyers, Cambridge (CA); Krishnaraj Tiwari, Guelph (CA); Jyoti Latawa, Mont-Royal (CA)

(73) Assignee: Her Majesty The Queen In Right of Canada, As Represented By The Minister of National Defence, Ottawa (CA)

( * ) Notice: Subject to any disclaimer, the term of this patent is extended or adjusted under 35 U.S.C. 154(b) by 0 days.

(21) Appl. No.: 16/464,797

(22) PCT Filed: Dec. 1, 2016

(86) PCT No.: PCT/CA2016/051412
§ 371 (c)(1),
(2) Date: May 29, 2019

(87) PCT Pub. No.: WO2018/098553
PCT Pub. Date: Jun. 7, 2018

(65) Prior Publication Data
US 2019/0284568 A1    Sep. 19, 2019

(51) Int. Cl.
*C12N 15/82* (2006.01)
*C07K 16/16* (2006.01)
*A61K 39/00* (2006.01)

(52) U.S. Cl.
CPC .......... *C12N 15/8258* (2013.01); *C07K 16/16* (2013.01); *C12N 15/8216* (2013.01); *A61K 2039/505* (2013.01); *C07K 2317/13* (2013.01); *C07K 2317/24* (2013.01); *C07K 2317/41* (2013.01); *C07K 2317/76* (2013.01)

(58) Field of Classification Search
None
See application file for complete search history.

(56) References Cited

U.S. PATENT DOCUMENTS

| 2014/0093504 A1 | 4/2014 | Hu et al. | |
| 2015/0368660 A1* | 12/2015 | Mason | C12N 15/8218 435/69.6 |

FOREIGN PATENT DOCUMENTS

| WO | 2004009618 A2 | 1/2004 | |
| WO | 2012167346 A1 | 12/2012 | |
| WO | WO-2012167346 A1 * | 12/2012 | ............. C07K 16/28 |

OTHER PUBLICATIONS

O'Hara et al. Plant-based expression of a partially humanized neutralizing monoclonal IgG directed against an immunodominant epitope on the ricin toxin A subunit. (2012) Vaccine; vol. 30; pp. 1239-1243 (Year: 2012).*
Foxwell et al. The use of anti-ricin antibodies to protect mice intoxicated with ricin. (1985) Toxicology; vol. 34; pp. 79-88 (Year: 1985).*
Maddaloni et al. Immunological characteristics associated with the protective efficacy of antibodies to ricin. (2004) J. or Immunology; vol. 172; pp. 6221-6228 (Year: 2004).*
Qiu et al. Effects of the sequence and orientation of an expression cassette in tobacco transformed by dual Bt genes. (2017) Plasmid; vol. 89; pp. 1-8; published online Nov. 15, 2016. (Year: 2017).*
O'Hara, J. M. et al. "Plant-Based Expression of a Partially Humanized Neutralizing Monoclonal IgG Directed Against an Immunodominant Epitope on the Rich Toxin A Subunit" Vaccine, Feb. 8, 2012, vol. 30, pp. 1239-1243.
Bakker, H. et al. "An Antibody Produced in Tobacco Expressing a Hybrid␣13-1,4 Galactosyltransferase is Essentially Devoid of Plant Carbohydrate Epitopes" Proc. Natl. Acad. Sci. U.S.A. Jun. 2006, vol. 103, pp. 7577-7582.
Garabagi, F. et al. "Utility of the P19 Suppressor of Gene-Silencing protein for production of Therapeutic Antibodies in Nicotiana Expression Hosts" Plant Biotech. J., Aug. 2012, vol. 10, pp. 1118-1128.
Wollacott, R. B. et al. "Analytical Characterization of a Monoclonal Antibody Therapeutic Reveals a Three-light Chain Species That Is Efficiently Removed Hydrophobic Interaction Chromatography" mAbs Nov./Dec. 2013, vol. 5, pp. 925-935.
Hu, Wei-Gang et al. "Anti-Ricin Efficacy Comparison of a Humanized Therapeutic Antibody Produced in Plants with Its Mammalian Cell-Produced Counterpart". Dec. 2015.
Smallshaw, Joan E. et al. "Ricin Vaccine Development" Current Topics in Microbiology and Immunology (2012) 357: 259-272 (Published Online Jul. 31, 2011).
Neal, Lori M. et al. "A Monoclonal Immunoglobulin G Antibody Directed against an Immunodominant Linear Epitope on the Ricin A chain Confers Systemic and Mucosal Immunity to Ricin" Infection and Immunity, Jan. 2010, p. 552-561.
Memari, Hamid Rajabi, et al. "Comparison of expression systems for the production of human interferon-a2b" Cent. Eur. J. Biol. 5(4), Mar. 2010, 446-455.
Lomonssoff, George P. et al. "Plant-produced biopharmaceuticals: A case of technical developments driving clinical deployment" Sep. 15, 2016, Science 353 (6305), p. 1237-1240.

(Continued)

*Primary Examiner* — Cathy Kingdon Worley
(74) *Attorney, Agent, or Firm* — Bereskin & Parr LLP/S.E.N.C.R.L., s.r.l.; Ainslie Parsons

(57) ABSTRACT

A method of making an antibody in plants that binds to ricin B chain is described. The method comprises (a) introducing a nucleic acid molecule encoding a heavy chain variable region of the antibody and a nucleic acid molecule encoding a light chain variable region of the antibody into a plant or plant cell; and (b) growing the plant or plant cell to obtain a plant that expresses the antibody or antibody fragment. The disclosure also relates to anti-ricin B chain antibodies and antibody fragments as well as methods of using same in therapy and prophylaxis.

7 Claims, 15 Drawing Sheets

Specification includes a Sequence Listing.

(56) References Cited

OTHER PUBLICATIONS

Lai, Huafang et al. "Monoclonal antibody produced in plants efficiently treats West Nile virus infection in mice" PNAS, Feb. 9, 2010, vol. 107, No. 6, 2419-2424.

Hu, Wei-Gang et al. "Humanization and Characterization of an Anti-Ricin Neutralization Monoclonal Antibody" PLoS ONE, Sep. 2012, 7(9), e45595.

He, Junyun et al. "Generation and Analysis of Novel Plant-Derived Antibody-Based Therapeutic Molecules against West Nile Virus" PLoS ONE, Mar. 2014, 9(3), e93541.

Chen, Qiang et al. The potential of plants as a system for the development and production of human biologies [versiobn 1; referees: 3 approved] F1000Research, May 2016, 5(F1000 Faculty Rev):912.

Audi, Jennifer et al. "Ricin Poisoning A Comprehensive Review" JAMA. Nov. 2005;294(18):2342-2351.

Streatfield, Stephen J. et al. "Plant-produced candidate countermeasures against emerging and reemerging infections and bioterror agents" Plant Biotechnology Journal (Aug. 2015) 13, pp. 1136-1159.

\* cited by examiner

A)

B)

C)

D)

A)

B)

Figure 5 con't
C)
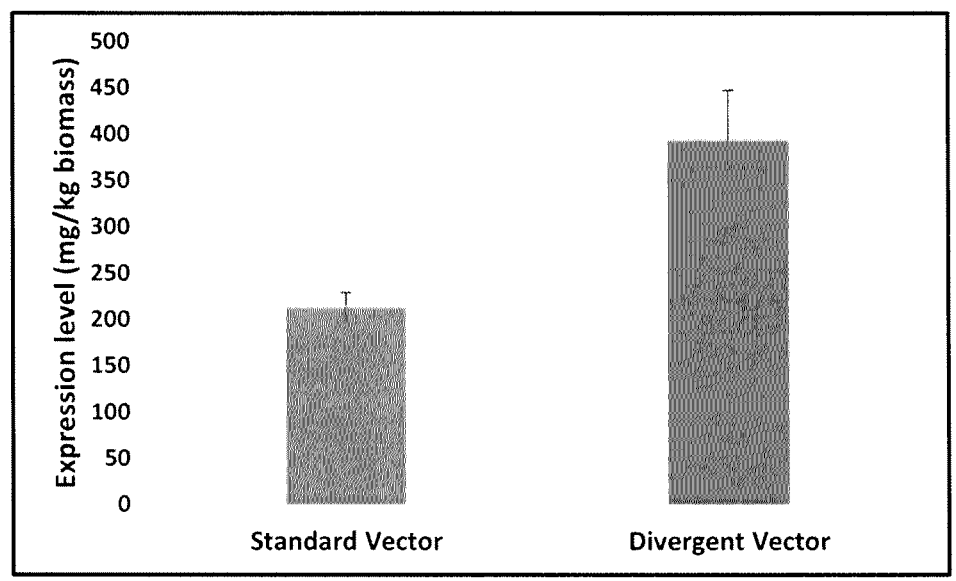

Figure 6 con't
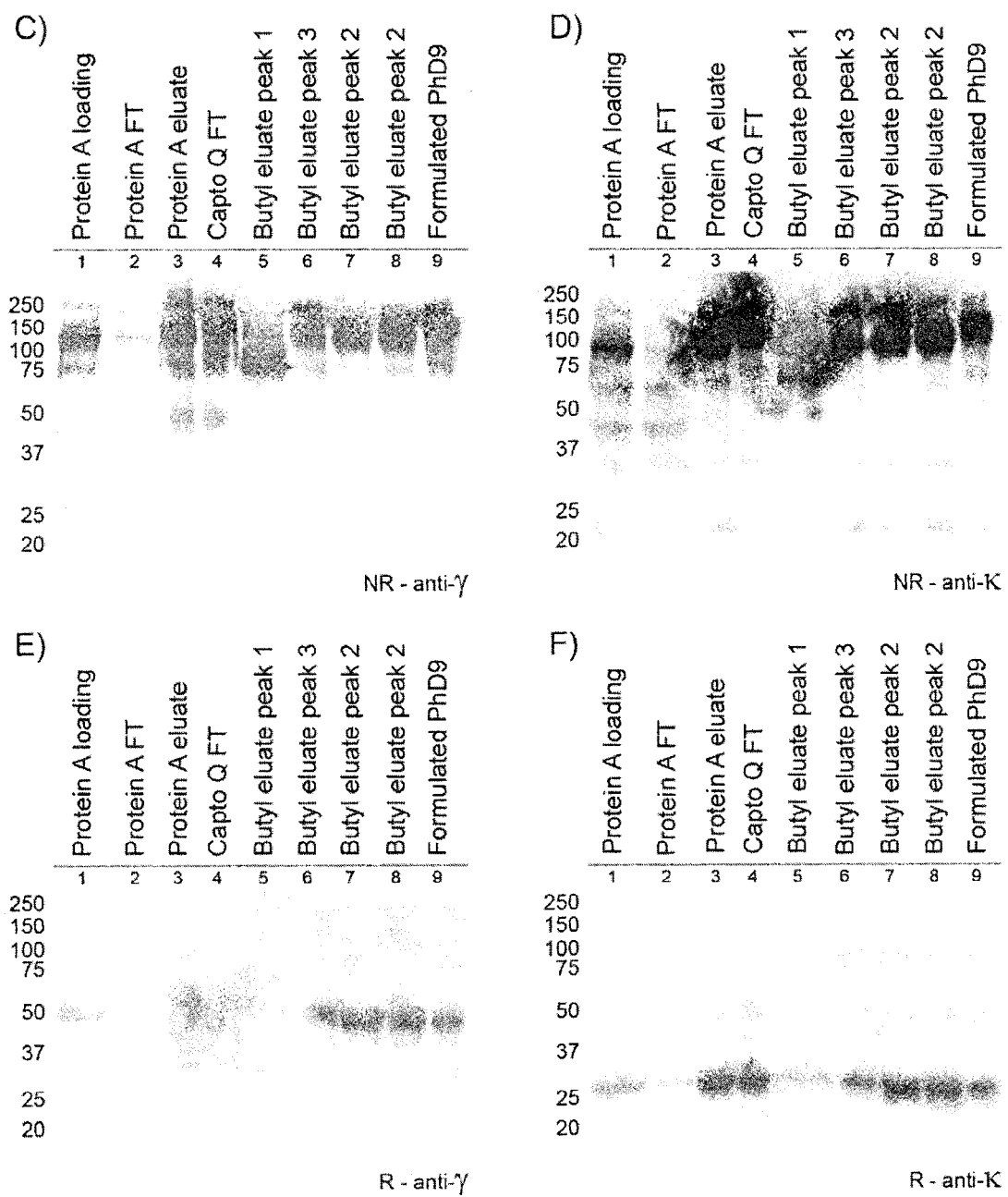

Figure 6 con't
G)
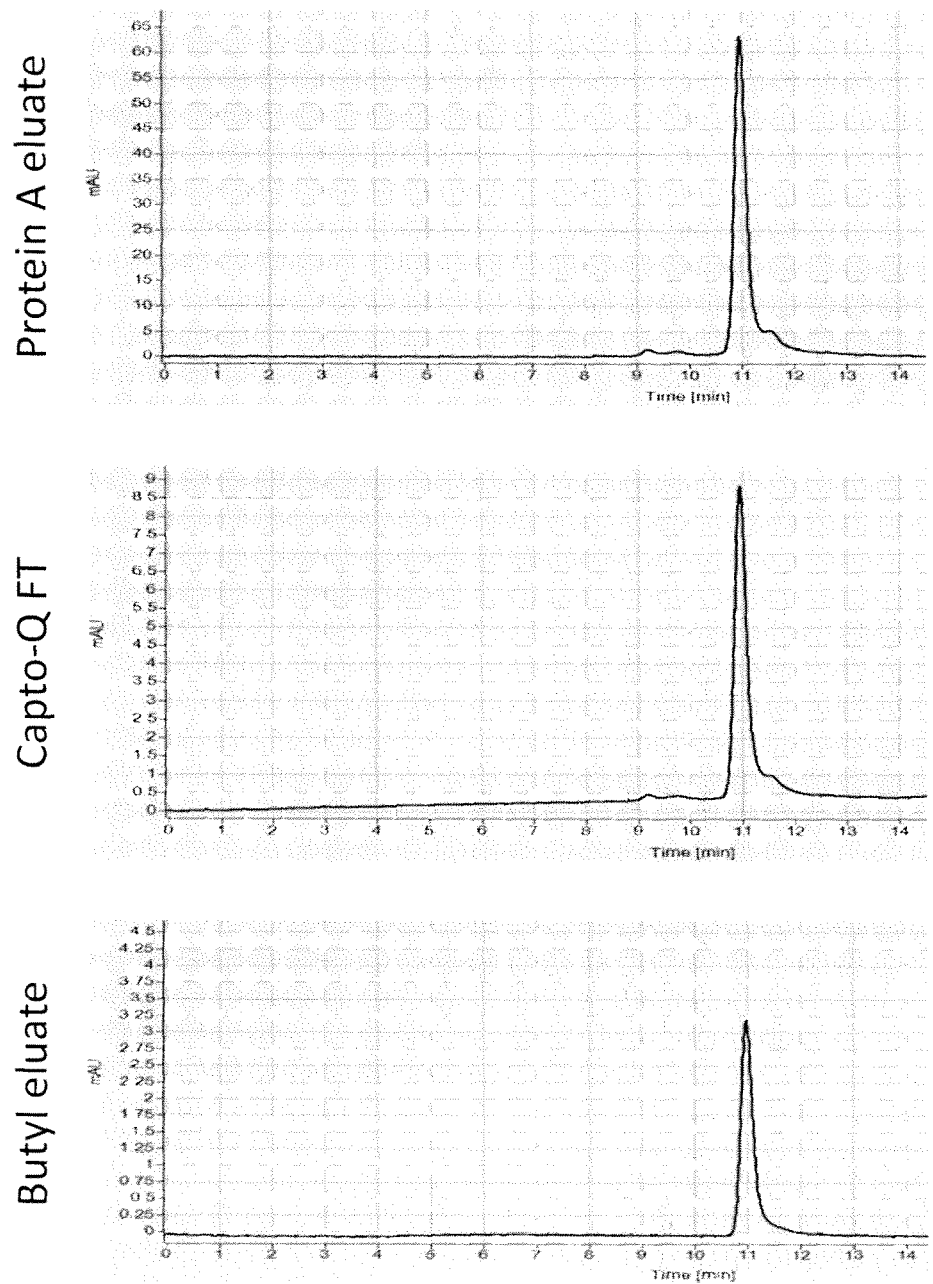

Figure 6 con't
H)
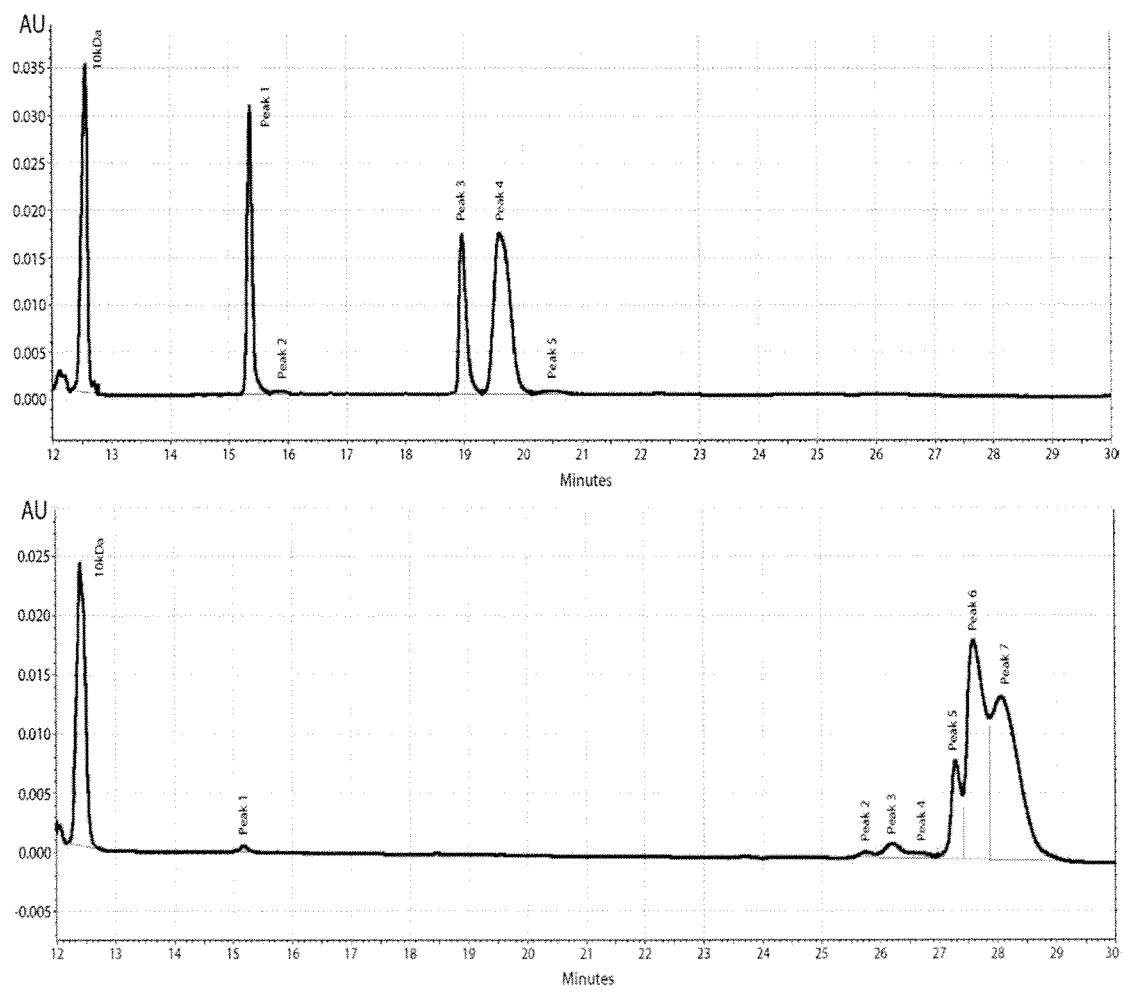

Figure 6 con't
l)

Figure 6 con't
J)
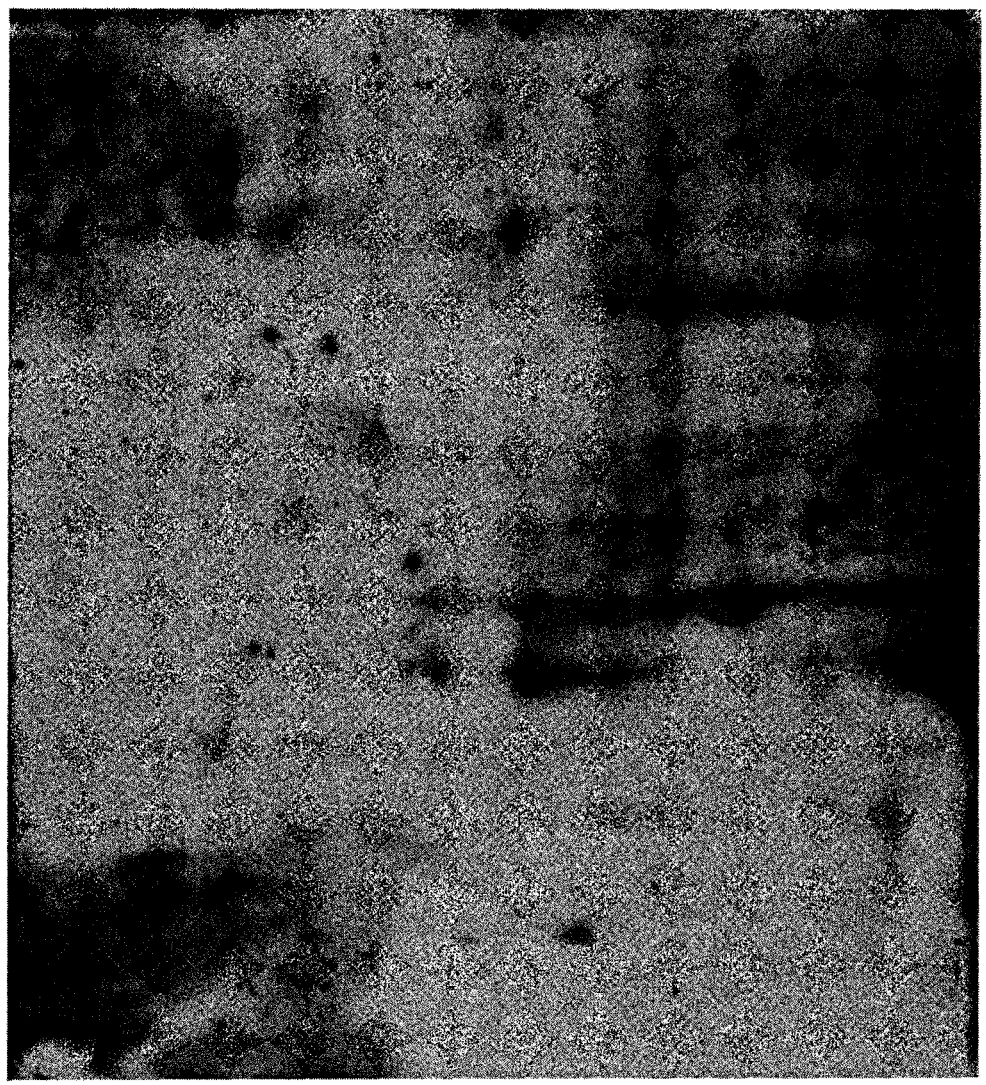

PRODUCTION IN PLANTS OF RICIN ANTIBODIES THAT BIND TO RICIN B CHAIN

CROSS-REFERENCE TO RELATED APPLICATION

This application is a nations' phase entry of PCT/CA2016/051412 filed Dec. 1, 2016 (which designates the U.S.).

INCORPORATION OF SEQUENCE LISTING

A computer readable form of the Sequence Listing "20436-P50330US00_SequenceListing.txt" (16,384 bytes), submitted via EFS-WEB and created on May 29, 2019, is herein incorporated by reference.

FIELD

The present disclosure relates to methods of making an antibody or antibody fragment that binds to ricin toxin lectin-B chain (ricin B chain) in a plant, the isolated antibodies or antibody fragments as well as methods of using the same in therapy and prophylaxis.

BACKGROUND

Ricin is a 60-65 kDa glycoprotein extracted from the common castor bean (*Ricinus communis*) and is regarded as a terrorist risk for the public due to its high toxicity and ease of production (Doan, 2004; Hu et al., 2012; Montanaro et al., 1973). Ricin is a simple toxin that consists of a ricin toxin enzymatic-A chain (ricin A chain) protein and a ricin B chain protein linked by a disulfide bond. By binding to specific sugar residues on the target cell surface, the ricin B chain serves as a key mediator for the internalization of the toxin via endocytosis. Once internalized, the ricin A chain enzymatically inactivates the ribosome to irreversibly inhibit protein synthesis. Even a single ricin A chain molecule within the cytoplasm of a cell will completely inhibit protein synthesis and result in cell death.

Ricin is among the deadliest known poisons. In mice, the $LD_{50}$ of ricin ingestion was reported to be 30 mg/kg bodyweight, and about 30 µg/kg by injection or inhalation (Audi et al., 2005). In human, $LD_{50}$ of ricin was estimated to be 1-20 mg/kg bodyweight by ingestion, and 1-20 µg/kg by injection or inhalation (Audi et al., 2005). The toxicity of ricin is 400 times higher than cobra venom, 1,000 times higher than cyanide, and 4,000 times higher than arsenic. The Centers for Disease Control and Prevention (Atlanta, USA) lists ricin as a Category B threat list and regards it as a high terrorist risk for civilians.

The development of an effective therapy against ricin has been fraught with difficulties. Chemical inhibitors targeting ricin have been identified but their applications have been limited by specificity, deliverability, and toxicity (Burnett et al., 2005; Miller et al., 2002). Development of vaccines against ricin is an ongoing endeavor, and there are two recombinant ricin A chain vaccines, RTA1-33/44-198 and RiVax, that are considered candidates for national vaccine stockpile (Smallshaw and Vitetta, 2012).

Amongst the myriad of approaches for countering ricin-induced lethality, anti-ricin antibodies appear to be the most promising treatment modality. Although antibodies against ricin can neutralize the toxin, currently there is no therapeutic antibody or vaccine available against ricin. Antibodies, whether polyclonal, monoclonal or fragments, have been developed against ricin A chain for blocking irreversible ribosomal inhibition, or against ricin B chain for preventing ricin from binding to and entering the cell (Neal et al., 2010; Foxwell et al., 1985). However, there are notable limitations in their potential application. For one, a considerable amount is necessary either to protect or treat a mouse from ricin poisoning. For example, about 50-100 µg of polyclonal antibodies (pAbs) (Foxwell et al., 1985; Hewetson et al., 1993) or 5-100 µg of monoclonal antibodies (mAbs) (Guo et al., 2006; Neal et al., 2010) per mouse are needed for protection. Also, there is a narrow window of time to apply the treatment. For example, 5 µg murine GD12 mAb delivered by the intra-peritoneal (i.p.) route had to be given within 24 hours to protect mice before $5×LD_{50}$ ricin challenge (Neal et al., 2010), while 100 µg of mAb per mouse had to be given within 30 minutes after $10×LD_{50}$ ricin challenge (Guo et al., 2006).

Therapeutic antibodies are among the most expensive drugs, in part due to extremely high production costs (estimated at least $300/gram) (Saunders et al., 2001). Traditionally, therapeutic mAbs have been produced in mammalian cell systems, but high production costs and time-consuming culturing processes hinder the efficiency of these systems (Birch and Racher, 2006; Roque et al., 2007). The high cost has dramatically affected the development of antibodies as therapeutics. In an attempt to meet rising market demands, pharmaceutical companies are working to improve the efficiency of existing biopharmaceutical production systems (Birch et al., 2006; Gagnon, 2012; Karg et al., 2009) as well as increase the number of antibody production facilities (Karg et al., 2009). Following construction, these facilities must be validated under Good Manufacturing Practice (GMP), a process that can take an average of three years (Vézina et al., 2009). Although some improvements have been made to increase antibody production, pharmaceutical companies still may not be able to meet future demands. As a result, alternative antibody expression systems are also being investigated (Birch et al., 2006; Karg et al., 2009).

Plant systems are fast, efficient, highly versatile for new product development, and easily scalable with significantly reduced manufacturing costs. Genetically modified plants offer an alternative to traditional mammalian cell expression systems for the large-scale production of therapeutic mAbs. In comparison to mammalian systems, genetically modified plants offer the advantages of lower upstream production costs, biological safety, ease of handling, and free from contamination by mammalian pathogens (Ko et al., 2009). Conversely, the limitations of genetically modified plants include the addition of plant-specific N-glycans to the recombinant antibodies and high downstream processing and purification costs.

Nonetheless, a wide variety of transgenic plant hosts have been successfully used for recombinant antibody production. Tobacco has been one of the most important plants used for antibody expression as it has a large biomass and is not a food crop. Full-length recombinant antibodies were first successfully expressed in tobacco plants in 1989 (Hiatt et al., 1989). Since then, the expression of antibodies in tobacco has been achieved using different expression platforms, including both stable and transient plant transformation technologies (Garabagi et al., 2012b; Giritch et al., 2006; Ko et al., 2009). Yet, despite the successful expression of antibodies in plants, there are currently no plant-produced antibodies that have been approved for human clinical therapy, saved for the exceptional circumstance surrounding ZMapp™, a plant-made mAb cocktail against Ebola, which was used experimentally to treat some patients with Ebola virus disease during the 2014-2016 West African Ebola outbreak (Chen and Davis, 2016). To achieve regulatory affirmation of plant-produced therapeutics, investigators must be able to demonstrate that plant-produced antibodies maintain the identical structural and functional integrity as their mammalian counterparts (Stöger et al., 2005). Plant-produced antibody preparations must also be analyzed to ensure that they are homogeneous, non-immunogenic and devoid of contaminants (Stöger et al., 2005). One study in mice has shown a plant-produced antibody to fight West Nile virus infection as equally well as its therapeutic counterpart (Lai et al., 2010).

An engineered version of murine GD12 mAb that targets ricin A chain has been produced in plants. The plant-derived version was a chimeric derivative of GD12 (cGD12), in which the murine heavy chain and light chain variable regions were fused to a human IgG1 framework, which was engineered and transiently expressed in *Nicotiana benthamiana* (O'Hara et al., 2012). Plant-produced cGD12 demonstrated epitope specificity and ricin neutralizing activity similar to those of the native murine mAb. In a post-exposure setting, the murine GD12 and chimeric cGD12 mAbs administered 6 hours after toxin challenge were each capable of rescuing mice from toxin-induced death.

Previously reported humanized recombinant antibody hD9 produced in mammalian cells demonstrated promising post-exposure therapeutic activity against ricin intoxication (Hu et al., 2012). A reduction in manufacturing cost for humanized recombinant antibody, for example by producing the antibody in plants, would be advantageous in the development of counter-ricin therapies.

SUMMARY

The present disclosure describes the successful expression of plant-produced anti-ricin B chain antibody hD9 (PhD9) in *N. benthamiana* using an *Agrobacterium tumefaciens*-based transient expression system. Both PhD9 and hD9 exerted a similar protective effect in in vitro and in vivo assays against ricin toxicity.

Accordingly, the present disclosure provides a method of making an antibody or antibody fragment in a plant that binds to ricin B chain comprising:

(a) introducing a nucleic acid molecule encoding a heavy chain variable region of the antibody and a nucleic acid molecule encoding a light chain variable region of the antibody into a plant or plant cell; and (b) growing the plant or plant cell to obtain a plant that expresses the antibody or antibody fragment.

In one embodiment, the method further comprises introducing a nucleic acid molecule encoding P19 suppressor of gene-silencing protein into the plant or plant cell.

In another embodiment, the method further comprises introducing a nucleic acid molecule encoding human 1,4-galactosyltransferase (GalT) into the plant or plant cell.

In one embodiment, the nucleic acid molecule encoding the heavy chain variable region and the nucleic acid molecule encoding the light chain variable region of the antibody are introduced on the same vector.

In another embodiment, the nucleic acid molecule encoding the heavy chain variable region and the nucleic acid molecule encoding the light chain variable region of the antibody are adjacent to each other in the vector in opposite and divergent transcriptional orientations.

In another embodiment, the nucleic acid molecule encoding the heavy chain variable region comprises a Complementarity Determining Region (CDR) H1 sequence as shown in SEQ ID NO:2, a CDR H2 sequence as shown in SEQ ID NO:3, and/or a CDR H3 sequence as shown in SEQ ID NO:4.

In another embodiment, the heavy chain variable region comprises the amino acid sequence of CDR H1 as shown in SEQ ID NO:6, CDR H2 as shown in SEQ ID NO:7, and/or CDR H3 as shown in SEQ ID NO:8.

In another embodiment, the nucleic acid molecule encoding the light chain variable region comprises a CDR L1 sequence as shown in SEQ ID NO:10, a CDR L2 sequence as shown in SEQ ID NO:11, and/or a CDR L3 sequence as shown in SEQ ID NO:12.

In another embodiment, the light chain variable region comprises the amino acid sequence of CDR L1 as shown in SEQ ID NO:14, CDR L2 as shown in SEQ ID NO:15, and/or CDR L3 as shown in SEQ ID NO:16.

In one embodiment, the nucleic acid molecule encoding the heavy chain variable region comprises a sequence as shown in SEQ ID NO:1, or a sequence at least 75% identical to SEQ ID NO:1 or the framework region thereof.

In another embodiment, the heavy chain variable region comprises the amino acid sequence as shown in SEQ ID NO:5, or a sequence at least 75% identical to SEQ ID NO:5 or the framework region thereof.

In one embodiment, the nucleic acid molecule encoding the light chain variable region comprises a sequence as shown in SEQ ID NO:9, or a sequence at least 75% identical to SEQ ID NO:9 or the framework region thereof.

In another embodiment, the light chain variable region comprises the amino acid sequence as shown in SEQ ID NO:13, or a sequence at least 75% identical to SEQ ID NO:13 or the framework region thereof.

In one embodiment, the nucleic acid sequence encoding the P19 suppressor of gene-silencing protein comprises a sequence as shown in SEQ ID NO:17, or a sequence at least 75% identical thereof.

In another embodiment, the P19 suppressor of gene-silencing protein comprises the amino acid sequence as shown in SEQ ID NO:18, or a sequence at least 75% identical thereof.

In one embodiment, the nucleic acid sequence encoding the human GalT comprises a sequence as shown in SEQ ID NO:19, or a sequence at least 75% identical thereof.

In another embodiment, the human GalT protein comprises the amino acid sequence as shown in SEQ ID NO:20, or a sequence at least 75% identical thereof.

In one embodiment, the plant is *N. benthamiana*.

In another embodiment, the antibody or antibody fragment is purified and polished by contacting the antibody or antibody fragment with Butyl HP resin.

The present disclosure also provides an antibody or antibody fragment prepared according to the methods described herein.

In one embodiment, the antibody or antibody fragment is an IgG1 antibody.

In another embodiment, the antibody or antibody fragment comprises a humanized glycosylation profile.

The present disclosure further provides a composition comprising an antibody or antibody fragment and a pharmaceutically acceptable diluent, excipient, or carrier.

In another embodiment, the composition is a vaccine composition.

The present disclosure in addition provides a method of preventing deleterious effects caused by ricin exposure or of treating exposure to ricin, comprising using or administering an antibody or antibody fragment or the composition described herein comprising an antibody or antibody fragment and a pharmaceutically acceptable diluent, excipient, or carrier to a subject in need thereof.

In one embodiment, the subject is a mouse, a rat, a non-human primate or a human.

In another embodiment, the antibody or antibody fragment is administered to the subject several hours following exposure to the ricin toxin to treat ricin exposure.

In another embodiment, the antibody or antibody fragment is administered to the subject several days or weeks prior to exposure to the ricin toxin to protect the subject against ricin exposure.

The present disclosure also provides a transgenic plant or plant cell that expresses an antibody that binds to ricin B chain comprising a nucleic acid molecule encoding a heavy chain variable region of the antibody, and a nucleic acid molecule encoding a light chain variable region of the antibody.

The one embodiment, the transgenic plant or plant cell that expresses an antibody that binds to ricin B chain further comprises a nucleic acid molecule encoding P19 suppressor of gene-silencing protein, and a nucleic acid molecule encoding human GalT.

In one embodiment, the heavy chain variable region comprises a CDR H1 sequence as shown in SEQ ID NO:6, a CDR H2 sequence as shown in SEQ ID NO:7, and/or a CDR H3 sequence as shown in SEQ ID NO:8; and the light chain variable region comprises a CDR L1 sequence as shown in SEQ ID NO:14, a CDR L2 sequence as shown in SEQ ID NO:15, and/or a CDR L3 sequence as shown in SEQ ID NO:16.

In another embodiment, the transgenic plant or plant cell comprises a nucleic acid sequence encoding the P19 suppressor of gene-silencing protein and/or a nucleic acid sequence encoding the human GalT.

In one embodiment, the antibody or antibody fragment that has been prepared in a plant binds to the ricin B chain.

In another embodiment, the nucleic acid molecules encoding the heavy chain and the light chain of PhD9 have been modified to incorporate plant codon-optimized codons.

In another embodiment, the suppressor of gene-silencing protein is encoded by the nucleic acid sequence of P19 suppressor of gene-silencing protein as shown in SEQ ID NO:17 or comprises the amino acid sequence of P19 suppressor of gene-silencing protein as shown in SEQ ID NO:18.

In another embodiment, the galactosyltransferase is encoded by the nucleic acid sequence of GalT as shown in SEQ ID NO:19, or comprises the amino acid sequence of GalT as shown in SEQ ID NO:20.

In addition, the present disclosure includes a scalable process to produce the anti-ricin antibody or antibody fragment comprising a humanized glycosylation profile.

Furthermore, the present disclosure includes methods of preventing deleterious effects caused by ricin exposure in pre-exposure prophylaxis or of treating exposure to ricin in post-exposure therapy.

Other features and advantages of the present disclosure will become apparent from the following detailed description. It should be understood, however, that the detailed description and the specific Example while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

Figure 1:
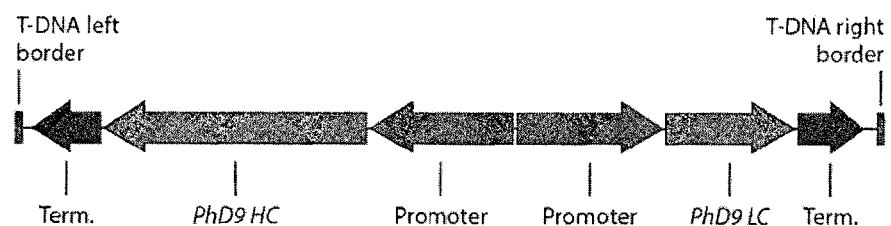
FIG. 1 shows T-DNA schematics for two PhD9 process vectors as set out in Example 1. (A) shows pPFC0904-hD9 HC ([−] orientation)/hD9 LC ([+] orientation), (B) shows pPFC1431-P19 ([+] orientation)/GalT ([+] orientation), (C) shows pPFC0811-P19 ([+] orientation) and (D) shows pPFC0901-hD9 HC ([+] orientation)/hD9 LC ([+] orientation).
Figure 1:
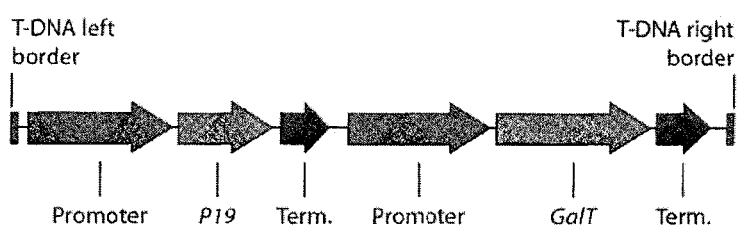
Figure 1:
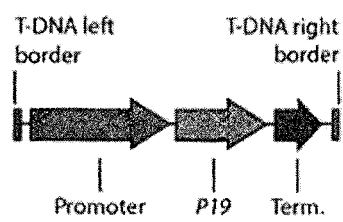
Figure 1:
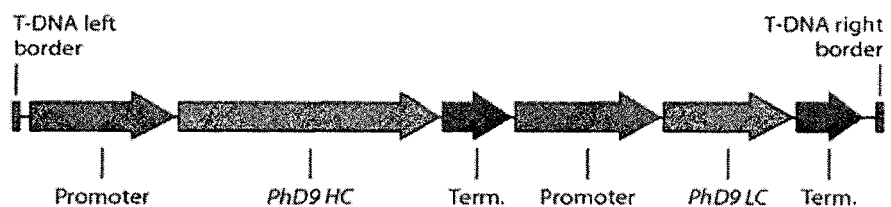

The plant hD9 (PhD9) anti-ricin B chain antibody was produced in transgenic *N. benthamiana* plants. *A. tumefaciens* clones carrying vectors expressing (1) P19 suppressor of gene-silencing protein, heavy and light hD9 IgG1 antibody chain genes, and (2) a human β1,4-galactosyltransferase gene were used to infiltrate transgenic *N. benthamiana* plants and a highly pure, low endotoxin, functionally active anti-ricin PhD9 antibody was obtained. The final PhD9 antibody contains <3% plant-specific glycans (β1,2-xylose or α1,3-fucose) by mass spectrometry. The purity of the PhD9 product is >94% based on capillary electrophoresis-SDS (CE-SDS) analysis. PhD9 binds to the ricin B chain in vitro, both by Western and ELISA. PhD9 is protective in an in vitro cell survival assay and an in vivo murine ricin challenge.

Accordingly, the present disclosure provides a method of making an antibody or antibody fragment in a plant that binds to ricin B chain comprising:

(a) introducing a nucleic acid molecule encoding a heavy chain variable region of the antibody and a nucleic acid molecule encoding a light chain variable region of the antibody into a plant or plant cell; and (b) growing the plant or plant cell to obtain a plant that expresses the antibody or antibody fragment.

As used herein, the term "antibody" refers to an immunoglobulin (Ig) molecule and immunologically active portions of an immunoglobulin molecule, i.e., molecules that contain an antigen binding site that specifically binds (immunoreacts with) an antigen. By "specifically bind", "immunoreacts with", or "directed against" is meant that the antibody reacts with one or more antigenic determinants of the desired antigen and does not react with other polypeptides or binds at much lower affinity ($K_d > 10^{-6}$). In one embodiment, PhD9 binds the ricin B chain with an affinity ($K_d$) of 1.77 nM. Antibodies include, but are not limited to, polyclonal antibodies, monoclonal antibodies, chimeric antibodies and humanized antibodies. The antibody may be from recombinant sources and/or produced in transgenic animals or plants.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

An "antibody fragment" as used herein may include any suitable antigen-binding fragment known in the art. The term "antibody fragment" includes, without limitation, Fv (a molecule comprising the VL and VH), single chain Fv (scFV; a molecule comprising the VL and VH connected by a peptide linker, Fab, Fab', F(ab')$_2$, dsFv, ds-scFv, single domain antibodies (sdAB; molecules comprising a single variable domain and 3 CDR), and multivalent presentations of these. Also included are dimers, minibodies, diabodies, and multimers thereof, and bispecific antibody fragments. The antibody fragment of the present disclosure may be obtained by manipulation of a naturally occurring antibody (such as, but not limited to) enzymatic digestion, or may be obtained using recombinant methods.

In general, antibody molecules obtained from humans relate to any of the classes IgG, IgM, IgA, IgE and IgD, which differ from one another by the nature of the heavy chain present in the molecule. Certain classes have subclasses as well, such as IgG1, IgG2 (further divided into IgG2a and IgG2b), IgG3 and IgG4. Furthermore, in humans, the light chain may be a kappa chain or a lambda chain. Accordingly, in one embodiment, the antibody disclosed herein is an IgG antibody, optionally an IgG1 antibody.

As used herein, the term "nucleic acid molecule" means a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

As used herein, the term "vector" means a nucleic acid molecule, such as a plasmid, comprising regulatory elements and a site for introducing transgenic DNA, which is used to introduce said transgenic DNA into a plant or plant cell. The transgenic DNA can encode a heterologous protein, which can be expressed in and isolated from a plant or plant cells. Vectors useful in the present methods are well known in the art. In one embodiment, the vector is a commercially-available vector. In another embodiment, the vector is pPFC0904, as described herein. In another embodiment, the vector is pPFC0904 or pPFC0901, as described herein.

As used herein, the term "expression cassette" means a single, operably linked set of regulatory elements that includes a promoter, a 5' untranslated region (5' UTR), an insertion site for transgenic DNA, a 3' untranslated region (3' UTR) and a terminator sequence.

As used herein, the term "glycosylation profile" means the characteristic "fingerprint" of the representative N-glycan species that have been released from a glycoprotein composition or glycoprotein product, either enzymatically or chemically, and then analyzed for their carbohydrate structure, for example, using LC-HPLC, or MALDI-TOF MS, and the like. See, for example, the review in Morelle and Michalski (2005).

As used herein, the term "humanized glycosylation profile" refers to a glycosylation profile that contains <5%, <4%, <3%, <2%, <1% or a negligible (non-measurable) amount of plant-specific glycans (β1,2-xylose and/or α1,3-fucose) as shown, for example, by mass spectrometry. The term "humanized glycosylation profile" also refers to a glycosylation profile that includes complex human-like N-glycans.

In one embodiment, the antibody or antibody fragment has a humanized glycosylation profile.

Any antibody or fragment thereof that binds the ricin B chain is contemplated by the present disclosure. By "binds the ricin B chain", it is meant that the antibody or fragment thereof of the present disclosure specifically recognizes and binds to the B chain of ricin. Ricin is a 60-65 kDa glycoprotein derived from beans of the castor plant. It is a relatively simple toxin compromising a ricin toxin enzymatic-A protein (the "ricin A chain") and a ricin toxin lectin-B protein (the "ricin B chain") linked by a disulphide bond. The ricin B chain is responsible for binding to specific sugar residues on the target cell surface and allows internalization of ricin by endocytosis, whereas the ricin A chain enzymatically inactivates the ribosome to irreversibly inhibit protein synthesis.

One example of an antibody that binds ricin B chain is antibody D9 or humanized D9 (hD9) as described in PCT publication no. WO/2012/167346. Other examples of antibodies that bind ricin B chain include, but are not limited to, antibodies A9, B10 and D3 as described in PCT publication no. WO/2012/167346.

Accordingly, in one embodiment of the present disclosure, the antibody is hD9 or a modified form thereof, consisting of 2 heavy chains and 2 light chains. The heavy chain will preferably have the amino acid sequence as shown in SEQ ID NO:5, or be encoded by the nucleic acid sequence as shown in SEQ ID NO:1. The light chain will preferably have the amino acid sequence as shown in SEQ ID NO:13, or be encoded by the nucleic acid sequence as shown in SEQ ID NO:9.

In one embodiment, the antibody or antibody fragment comprises the amino acid sequence of the heavy chain variable region shown in SEQ ID NO:5. In another embodiment, the antibody or antibody fragment comprises a heavy chain variable region comprising a CDR H1 sequence as shown in SEQ ID NO:6, a CDR H2 sequence as shown in SEQ ID NO:7, and/or a CDR H3 sequence as shown in SEQ ID NO:8. In another embodiment, the antibody or antibody fragment comprises the amino acid sequence of the light chain variable region shown in SEQ ID NO:13. In another embodiment, the antibody or antibody fragment comprises a light chain variable region comprising a CDR L1 sequence as shown in SEQ ID NO:14, a CDR L2 sequence as shown in SEQ ID NO:15, and/or a CDR L3 sequence as shown in SEQ ID NO:16.

The region of the heavy chain or light chain variable region outside of the CDR is referred to as the framework region (FR). The FR provides structural integrity to the variable domain and ensures retention of the immunoglobulin fold. This characteristic structure of antibodies provides a stable scaffold upon which substantial antigen-binding diversity can be explored by the immune system to obtain specificity for a broad array of antigens (Padlan, 1994). The FR of the variable domain generally shows less sequence variability than the hypervariable regions.

As used here, the term "sequence identity" refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions multiplied by 100%). In one embodiment, the two sequences are the same length. The determination of percent identity between two sequences can also be accomplished using a mathematical algorithm. One non-limiting example of a mathematical algorithm utilized for the comparison of two sequences is the algorithm of Karlin and Altschul (1990), modified as in Karlin and Altschul (1993). Such an algorithm is incorporated into the NBLAST and XBLAST programs of Altschul et al. (1990). BLAST nucleotide searches can be performed with the NBLAST nucleotide program parameters set, e.g., for score=100, wordlength=12 to obtain nucleotide sequences homologous to a nucleic acid molecules of the present disclosure. BLAST protein searches can be performed with the XBLAST program parameters set, e.g., to score=50, wordlength=3 to obtain amino acid sequences homologous to a protein molecule of the present disclosure. To obtain gapped alignments for comparison purposes, Gapped BLAST can be utilized as described in Altschul et al. (1997). Alternatively, PSI-BLAST can be used to perform an iterated search which detects distant relationships between molecules (Altschul et al., 1997). When utilizing BLAST, Gapped BLAST, and PSI-Blast programs, the default parameters of the respective programs (e.g., of XBLAST and NBLAST) can be used (see, e.g., the NCBI website). Another non-limiting example of a mathematical algorithm utilized for the comparison of sequences is the algorithm of Myers and Miller (1988). Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

The sequences of the present disclosure may be at least 75% identical to the sequences described herein; in another example, the sequences may be at least 70%, 75%, 80%, 85%, 86%, 87%, 88%, 89%, 90%, 91%, 92%, 93%, 94%, 95%, 96%, 97%, 98%, 99%, or 100% identical at the nucleic acid or amino acid level to sequences described herein. Importantly, the proteins encoded by the variant sequences retain the activity and specificity of the proteins encoded by the reference sequences. As would be known to one of skill in the art, amino acid residues of an antibody, particularly within the framework regions may be mutated (for example, by conservative substitution) without significantly affecting the functional properties of the antibody (antigen recognition and binding).

Also provided is an amino acid sequence of a heavy chain variable region with at least 70%, 75%, 80%, 85%, 86%, 87%, 88%, 89%, 90%, 91%, 92%, 93%, 94%, 95%, 96%, 97%, 98%, 99%, or 100% sequence identity to SEQ ID NO:5 or to the framework region of SEQ ID NO:5. Also provided is an amino acid sequence of a light chain variable region with at least 70%, 75%, 80%, 85%, 86%, 87%, 88%, 89%, 90%, 91%, 92%, 93%, 94%, 95%, 96%, 97%, 98%, 99%, or 100% sequence identity to SEQ ID NO:13 or to the framework region of SEQ ID NO:13.

Also provided is a nucleic acid encoding a heavy chain variable region with at least 70%, 75%, 80%, 80%, 85%, 90%, 95%, 98%, 99% or 100% sequence identity to SEQ ID NO:1 or to the framework region of SEQ ID NO:1. Also provided is a nucleic acid encoding a light chain variable region with at least 70%, 75%, 80%, 80%, 85%, 90%, 95%, 98%, 99% or 100% sequence identity to SEQ ID NO:9 or to the framework region of SEQ ID NO:9. Also provided is a nucleic acid encoding P19 suppressor gene-silencing protein with at least 70%, 75%, 80%, 80%, 85%, 90%, 95%, 98%, 99% or 100% sequence identity to SEQ ID NO:17. Also provided is a nucleic acid encoding human GalT with at least 70%, 75%, 80%, 80%, 85%, 90%, 95%, 98%, 99% or 100% sequence identity to SEQ ID NO:19.

Nucleic acid and amino acid sequences described herein are set out in Table 1.

In one embodiment, a vector is provided encoding both a heavy chain variable region and a light chain variable region as described herein. In another embodiment, a vector is provided encoding a heavy chain variable region, a light chain variable region and P19 as described herein. In yet another embodiment, a vector is provided encoding a heavy chain variable region, a light chain variable region, P19 and human GalT as described herein.

P19 is a viral protein that suppresses gene silencing. For example, P19 from Tomato bushy stunt virus (TBSV) is an example of a protein known to function as a potent suppressor of gene silencing in plants as well as in animals (for example, Accession No. NP_062901.1; Garabagi et 2012b). A nucleic acid sequence and an amino acid sequence of P19 from TBSV are provided herein as SEQ ID NOs: 17 and 18, respectively.

"GalT" as used herein refers to beta-1,4-galactosyltransferase (for example, Accession No. NP_001488.2). A nucleic acid sequence and an amino acid sequence of human GalT ($\beta$1,4-galactosyltransferase (B4GalT1)) are provided herein as SEQ ID NOs: 19 and 20, respectively.

In another embodiment, a vector is provided encoding a nucleic acid molecule encoding a heavy chain variable region and a nucleic acid molecule encoding a light chain variable region of the antibody, and the two nucleic acid molecules are adjacent to each other in the vector in opposite and divergent transcriptional orientations.

As used herein, the term "opposite and divergent transcriptional orientations" means that the sequence of a first nucleic acid molecule is transcribed 5' to 3' from one strand of the DNA (e.g., the bottom strand) and the sequence of a second nucleic acid molecule is transcribed 5' to 3' from the other stand of the DNA (e.g., the top strand), resulting in bidirectional transcription (i.e. divergent directions) away from the promoter sequences.

In one embodiment, the PhD9 heavy chain and light chain nucleic acid molecules are positioned adjacent to each other on the same vector, wherein opposite and divergent transcriptional orientations of the two nucleic acid molecules results in at least a 0.5 fold, 1 fold, 1.5 fold, two-fold or three-fold increase in PhD9 expression levels in total soluble protein extracts relative to the same two nucleic acid molecules in the same transcriptional orientation. Further, the percentage of intact IgG1 following Protein A purification increased from ca. 50% to ca. 80% according to area under the curve analysis of size exclusion chromatography. Accordingly, in another embodiment, the percentage of intact IgG1 increases by at least 10%, 20%, 30%, 40%, 50%, 60%, 70%, 80%, 90% or 100% when the PhD9 heavy chain and light chain nucleic acid molecules are positioned adjacent to each other on the same vector in an opposite and divergent transcriptional orientation as compared to when they are positioned in the same transcriptional orientation.

In one embodiment, a signal peptide may be placed at the amino (N-) termini of the heavy chain and/or light chain. In a specific embodiment, the Arabidopsis thaliana basic chitinase signal peptide (SP) (Samac et al., 1990), namely MAKTNLFLFLIFSLLLSLSSA (SEQ ID NO:21), is placed at the N-termini of the heavy and light chains (Samac et al., 1990).

Other signal peptides can be mined from GenBank (see world wide web at ncbi.nlm.nih.gov/genbank) or other such databases, and their sequences added to the N-termini of the heavy chain or light chain, nucleic acid sequences for these being optimized for plant-preferred codons as described above and then synthesized. The functionality of a SP sequence can be predicted using online freeware such as the SignalP program (see world wide web at cbs.dtu.dk/services/SignalP).

In a specific embodiment, the nucleic acids are optimized for plant codon usage. In particular, the nucleic acid sequence encoding the heavy chain and light chain can be modified to incorporate codon-optimized plant codons. In a specific embodiment, coding sequences for both the heavy chain and light chain, including the SP in both cases, are optimized for expression in Nicotiana species with the goal of making the coding sequences more similar to those of Nicotiana species. Codon optimizations may be performed as known in the art, for example by utilizing online freeware, the Protein Back Translation program (Entelechon), and Nicotiana coding sequence preferences. Codons with the highest frequencies for each amino acid in Nicotiana species (Nakamura, 2005) are thereby incorporated. Furthermore, potential intervening sequence splice-site acceptor and donor motifs can be identified (Shapiro et al., 1987; CNR National Research Council) and subsequently removed by replacement with nucleotides that resulted in codons encoding the same amino acids. Inverted repeat sequences can be analyzed using the Genebee RNA Secondary Structure software package (Brodsky et al., 1995; GeneBee Molecular Biology Server); nucleotides can be changed to reduce the free energy (kilocalories per mole) of potential secondary structure while maintaining the polypeptide sequence. Likewise, repeated elements can be analyzed (CNR National Research Council) and replaced where present. Potential methylation sites (i.e., CXG and CpG; Gardiner-Garden et al., 1987) can be replaced where possible and always without changing the encoded amino acid sequence. A Kozak (Kozak, 1984) optimized translation start site can be engineered. Plant polyadenylation sites (i.e., AATAAA, AATGAA, AAATGGAAA, and AATGGAAATG (Li et al., 1995; Rothnie, 1996) and ATTTA RNA instability elements (Ohme-Takagi et al., 1993) can be likewise avoided.

The coding sequences for the heavy chain and light chain, including codons for the Arabidopsis basic chitinase SP, and P19 suppressor of gene-silencing protein and human GalT, are optionally synthesized using standard procedures (for example, Almquist et al., 2004; Almquist et al., 2006; McLean et al., 2007; Olea-Popelka et al., 2005). In one embodiment, the entire SP-heavy chain coding sequence and the entire SP-light chain coding sequence are subcloned into a vector, for example p105T-based vector pDAO19 to generate pPFC0901 and pPFC0904. In another embodiment, coding sequences may be subcloned into the pFBin vector.

The nucleic acid vectors encoding the heavy chain variable region and/or the light chain variable region (and optionally the constant regions for both) can also contain other elements suitable for the proper expression of the antibodies or antibody fragments in the plant or plant cell. In particular, each vector can also contain a promoter that promotes transcription in plants or plant cells. Suitable promoters include, but are not limited to, cauliflower mosaic virus promoters (such as CaMV35S and 19S), nopaline synthase promoters, alfalfa mosaic virus promoter, and other plant virus promoters. Constitutive promoters, such as plant actin gene promoters, and histone gene promoters can also be used.

Inducible promoters, such as light-inducible promoters: ribulose-1,5-bisphosphate carboxylase oxidase (a.k.a. RUBISCO) small subunit gene promoter; chlorophyll a/b binding (CAB) protein gene promoter; and other light inducible promoters may also be used. Other inducible promoters include chemically-inducible promoters, alcohol inducible promoters, and estrogen inducible promoters.

Synthetic promoters, such as the so-called superpromoter comprised of 3 mannopine synthase gene upstream activation sequences and the octopine synthase basal promoter sequence (Lee et al., 2007) can also be used.

Predicted promoters, such as those that can be found from genome database mining (Shahmuradov et al., 2003) may also be used.

The nucleic acid vectors can also contain suitable terminators useful for terminating transcription in the plant or plant cell. Examples of terminators include the nopaline synthase poly A addition sequence (nos poly A), cauliflower mosaic virus 19S terminator, actin gene terminator, alcohol dehydrogenase gene terminator, or any other terminator from the GenBank database.

The nucleic acid vectors may also include other components such as signal peptides that direct the polypeptide to the secretory pathway of plant cells, such as the *Arabidopsis thaliana* basic chitinase SP (Samac et al., 1990) as described above.

Seletectable marker genes can also be linked on the T-DNA, such as the kanamycin resistance gene (also known as neomycin phosphotransferase gene II, or nptII), Basta resistance gene, hygromycin resistance gene, or others.

In one embodiment, the nucleic acid molecule encoding a heavy chain variable region, the nucleic acid molecule encoding a light chain variable region, the nucleic acid molecule encoding human GalT and the nucleic acid molecule encoding P19 suppressor of gene-silencing gene may be introduced into the plant or plant cell on separate vectors.

In another embodiment, the nucleic acid molecule encoding a heavy chain variable region and the nucleic acid molecule encoding a light chain variable region are introduced on the same vector, wherein the nucleic acid molecule encoding a heavy chain variable region and the nucleic acid molecule encoding a light chain variable region of the antibody are adjacent to each other in opposite and divergent transcriptional orientations such that higher levels of protein expression of the heavy chain variable region and the light chain variable region are produced relative to identically situated vector having the nucleic acid molecule encoding a heavy chain variable region and the nucleic acid molecule encoding a light chain variable region in the same transcriptional direction.

In another embodiment, the nucleic acid molecule encoding the heavy chain variable region and the nucleic acid molecule encoding the light chain variable region may be introduced into the plant or plant cell on the same nucleic acid vector. The nucleic acid molecule encoding human GalT may be introduced into the plant or plant cell on a separate nucleic acid vector. The nucleic acid molecule encoding P19 suppressor of gene-silencing gene may be introduced into the plant or plant cell on another separate nucleic acid vector.

In another embodiment, the nucleic acid molecule encoding P19 suppressor of gene-silencing gene, and the nucleic acid molecule encoding human GalT may be introduced into the plant or plant cell on the same nucleic acid vector.

In another embodiment, the nucleic acid molecule encoding the heavy chain variable region, the nucleic acid molecule encoding the light chain variable region, and the nucleic acid molecule encoding P19 suppressor of gene-silencing gene may be introduced into the plant or plant cell on the same nucleic acid vector. The nucleic acid molecule encoding human GalT may be introduced into the plant or plant cell on a separate nucleic acid vector.

In another embodiment, the nucleic acid molecule encoding the heavy chain variable region, the nucleic acid molecule encoding the light chain variable region, and the nucleic acid molecule encoding human GalT may be introduced into the plant or plant cell on the same nucleic acid vector. The nucleic acid molecule encoding P19 suppressor of gene-silencing gene may be introduced into the plant or plant cell on a separate nucleic acid vector.

In yet another embodiment, the nucleic acid molecule encoding the heavy chain variable region, the nucleic acid molecule encoding the light chain variable region, the nucleic acid molecule encoding P19 suppressor of gene-silencing gene, and the nucleic acid molecule encoding human GalT may be introduced into the plant or plant cell on the same nucleic acid vector.

The phrase "introducing a nucleic acid molecule into a plant or plant cell" includes both the stable integration of the nucleic acid molecule into the genome of a plant cell to prepare a transgenic plant or plant cell as well as the transient integration of the nucleic acid into a plant or part thereof.

The nucleic acid vectors may be introduced into the plant or plant cell using techniques known in the art including, without limitation, electroporation, an accelerated particle delivery method, a cell fusion method or by any other method to deliver the nucleic acid vectors to a plant or plant cell, including *Agrobacterium* mediated delivery, or other bacterial delivery such as *Rhizobium* sp. NGR234, *Sinorhizobium meliloti* and *Mesorhizobium loti* (Chung et al., 2006).

The plant or plant cell may be any plant or plant cell, including, without limitation, tobacco plants or plant cells, tomato plants or plant cells, maize plants or plant cells, alfalfa plants or plant cells, *Nicotiana benthamiana*, rice plants or plant cells, *Lemna major* or *Lemna minor* (duckweeds), safflower plants or plant cells or any other plants or plant cells that are both agriculturally propagated and amenable to genetic modification for the expression of recombinant or foreign proteins.

The phrase "growing a plant or plant cell to obtain a plant that expresses the antibody or antibody fragment" includes both growing transgenic plant cells into a mature plant as well as growing or culturing a mature plant that has received the nucleic acid molecules encoding the antibody. One of skill in the art can readily determine the appropriate growth conditions in each case.

In a specific embodiment, plasmids containing the nucleic acid molecules are introduced into *A. tumefaciens* strain by electroporation procedures. The *N. benthamiana* plants can be vacuum infiltrated according to the protocol described by Marillonnet et al. (2005), Giritch et al. (2006) and Garabagi et al. (2012a) with several modifications. Briefly, all cultures can be grown at 28° C. and 220 rpm to a final optical density at 600 nm ($OD_{600}$) of 1.8 or 2.0. In one embodiment, equal volumes are combined and pelleted by centrifugation at 8,000 rpm for 4 minutes, resuspended and diluted by $10^3$ in infiltration buffer (10 mM 1-(N-morpholino)ethanesulphonic acid (MES), pH 5.5, 10 mM $MgSO_4$). Alternatively, each of the *Agrobacterium* cultures could be grown to lower OD values and Beer's Law could be applied to determine the volumes of each culture required to make a bacterial suspension cocktail whereby the concentrations of each bacterial strain were equivalent. Alternatively, higher or lower dilutions with infiltration buffer could be used.

In another specific embodiment, the aerial parts of five-week-old *N. benthamiana* plants are submerged in a chamber containing the *A. tumefaciens* resuspension solution, after which a vacuum (0.5 to 0.9 bar) is applied for 90 seconds followed by a slow release of the vacuum, after which plants were returned to the greenhouse for 7 days before being harvested. In another embodiment, older or younger plants are used. In further embodiments, longer or shorter periods under vacuum, and/or vacuum release and/or longer or shorter periods of growth in greenhouse are used. Standard horticultural improvements of growth, maximized for recombinant protein production can also be used (see Colgan et al., 2010).

In another embodiment, instead of transient introduction of vectors (for example, pPFC0811, pPFC0901, pPFC0904, and/or pPFC1431-based vectors) containing the PhD9 heavy chain, light chain, P19 suppressor of gene-silencing protein and/or human GalT coding sequences, stable transgenic plants or plant cells are made. In one embodiment, one vector is used on which the nucleic acid molecule encoding the heavy chain variable region, the nucleic acid molecule encoding the light chain variable region, P19 suppressor of gene-silencing protein and human GalT are introduced together on the same vector.

In another embodiment, the nucleic acid molecule encoding the heavy chain, the nucleic acid molecule encoding the light chain and P19 suppressor of gene-silencing protein are introduced into the plant or plant cell on one nucleic acid vector, and the nucleic acid molecule encoding the human GalT is introduced into the plant cell on a separate nucleic acid vector. In such an embodiment, the heavy chain, the light chain and P19 suppressor of gene-silencing protein would be expressed from one transgenic locus and the human GalT would be expressed from a different transgenic locus.

In another embodiment, plant expression vector(s) containing antibody heavy chain and light chain genes are introduced into *Agrobacterium tumefaciens* At542 or other suitable *Agrobacterium* isolates such as At564, or other suitable bacterial species capable of introducing DNA to plants for transformation such as *Rhizobium* sp., *Sinorhizobium meliloti, Mesorhizobium loti* and other species (Broothaerts et al. 2005; Chung et al., 2006), by electroporation or other bacterial transformation procedures. *Agrobacterium* clones containing vectors can be propagated on Luria-Bertani (LB) plates containing rifampicin (30 mg/L) and kanamycin (50 mg/L), or other selectable media, depending on the nature of the selectable marker genes on the vector. *Agrobacterium*-mediated leaf disk transformation (Gelvin, 2003; Horsch et al. 1985), or similar protocols involving wounded tobacco (*N. tabacum*, variety 81V9 or tissue of other tobacco varieties such as those listed in Conley et al., 2009) or *N. benthamiana* or other plant species such as those of the *Solanaceae*, maize, safflower, *Lemna* spp., etc. can be infected with the *Agrobacterium* culture ($OD_{600}$=0.6) and plated on Murashige and Skoog plus vitamins medium (MS; Sigma), supplemented with agar (5.8%; Sigma) and containing kanamycin (100 mg/L) or 500 cefotaxime (mg/L) or other selectable media, depending on the nature of the selectable marker genes on the vector, for selection of transformed plant cells. Production of shoots can be induced with naphthalene acetic acid (NAA; 0.1 mg/L; Sigma) and benzyl adenine (BA; 1 mg/L; Sigma) in the medium. For induction of roots, the newly formed shoots were moved to Magenta boxes (Sigma-Aldrich, Oakville, ON) on MS medium (as above) that was lacking NAA and BA. After roots are formed, plants can be transplanted to soil and could be raised in greenhouse culture. For plant transformation, as many as possible or at least 25 primary transgenic plants can be produced. ELISA and quantitative immunoblots can be performed on each plant to characterize levels of total and active antibody produced by the plants, respectively (Almquist et al., 2004; Almquist et al., 2006; Makvandi-Nejad et al., 2005; McLean et al., 2007; Olea-Popelka et al., 2005).

In another embodiment, after selection of antibody expressing primary transgenic plants, or concurrent with selection of antibody expressing plants, derivation of homozygous stable transgenic plant lines is performed. Primary transgenic plants can be grown to maturity, allowed to self-pollinate, and produce seed. Homozygosity can be verified by the observation of 100% resistance of seedlings on kanamycin plates (50 mg/L), or other selectable drug as indicated above. A homozygous line with single T-DNA insertions, that are shown by molecular analysis to produce most amounts of antibody, can be chosen for breeding to homozygosity and seed production, ensuring subsequent sources of seed for homogeneous production of antibody by the stable transgenic or genetically modified crop (McLean et al., 2007; Olea-Popelka et al., 2005; Yu et al., 2008).

The antibody or antibody fragment may be purified or isolated from the plants using techniques known in the art, including homogenization, clarification of homogenate and affinity purification. Homogenization is any process that crushes or breaks up plant tissues and cells and produces homogeneous liquids from plant tissues, such as using a blender, or juicer, or grinder, or pulverizer such as mortar and pestle, etc. Clarification involves either/and/or centrifugation, filtration, etc. Affinity purification uses Protein A, Protein G, Protein L, and/or antibodies that bind antibodies.

As used herein, the term "polishing" refers to post-purification removal of aggregates, endotoxin, DNA, viruses and any other impurities and contaminants in the preparation of an antibody or antibody fragment.

In another embodiment, the antibody is purified and polished by contacting Butyl HP resin. Homogenate is clarified through several stages to remove gradually smaller particulate matter. Clarified extract is applied to a Protein A column. The Protein A eluate is applied to a Capto-Q column in flow-through mode. The Capto-Q flow-through is then applied to a Butyl HP resin column. The butyl eluate is then fill-finished.

The present disclosure also includes compositions of matter and uses thereof, or antibodies or antibody fragments and uses thereof.

The present disclosure further includes a transgenic plant that expresses an antibody that binds to ricin B chain comprising a nucleic acid molecule encoding a heavy chain variable region, a nucleic acid encoding a light chain variable region of the antibody, a nucleic acid encoding P19 suppressor of gene-silencing protein, and a nucleic acid encoding the human GalT.

The present disclosure also includes an antibody or antibody fragment prepared according to the methods described herein. In one embodiment, the antibody comprises the heavy chain variable region shown in SEQ ID NO:5 and the light chain variable region shown in SEQ ID NO:13.

The present disclosure includes all uses of the antibodies or antibody fragments prepared according to the methods described herein, including, without limitation, the use or a method of preventing deleterious effects caused by ricin exposure or of treating exposure to ricin to a subject in need thereof. The subject in need of the use of the antibodies or antibody fragments is optionally a rodent (including but not limited to mice (*Mus*) and rats (*Rattus*)), a human, a non-human primate, a *Canis*, a *Felis*, an *Equus*, an *Ovis*, a *Capra*, a *Sus*, a *Gallus*, an *Anas*, an *Anatidae*, a *Leporidae*, a *Bos*, a *Bubalus*, a *Columba*, a *Meleagris*, a *Cairina*, an *Oryctolagus* or a *Carassius*.

Accordingly, the present disclosure provides a method of preventing or treating ricin exposure, ricin-induced toxicity and ricin-induced lethality comprising using or administering an effective amount of an antibody or antibody fragment prepared in a plant as described herein. The disclosure also provides a use of an effective amount of an antibody or antibody fragment prepared in a plant for preventing or treating ricin exposure, ricin-induced toxicity and ricin-induced lethality in a subject in need thereof.

The use or administration of antibodies or antibody fragments to a subject comprising ingestion, inhalation, or injection. The route of injection includes but not limited to intradermal, subcutaneous, intramuscular, intravenous, intraosseous, intraperitoneal, intrathecal, epidural, intracardiac, intraarticular, intracavernous, intravitreal, intracerebral, intracerebroventricular, or intraportal.

The use of administration of antibodies or antibody fragments to a subject is carried out several hours following exposure to the ricin toxin to treat ricin exposure, or several days or weeks prior to exposure to the ricin toxin to protect the subject against ricin exposure.

The following non-limiting Example is illustrative of the present disclosure:

Example 1

Experimental Procedures
A. Preparation of Ricin Stock

Ricin was prepared from castor bean seeds in Defense Research and Development Canada-Suffield. The toxicity of ricin stock was also determined. One $LD_{50}$ of ricin for mice was determined by the i.p. injection of a series of ricin dilution into mice. The mice were observed for 7 days. The amount of ricin for 1×$ED_{50}$ delivered by the i.p. route for one 20-25 gram female Balb/c mouse was 0.215 μg, 5×$LD_{50}$ was 1.075 μg, or about 1 μg. For 5×$LD_{50}$ of ricin delivered by the i.p. route, mice died within 1-2 days.
B. Expression Vectors Two *Agrobacterium tumefaciens* transfer DNA (T-DNA) vectors were employed for the production of galactosylated plant hD9 (PhD9) monoclonal antibody (mAb). FIG. 1A shows one T-DNA vector expresses the PhD9 light chain (LC) and PhD9 heavy chain (HC) in divergent directions. FIG. 1B shows a second T-DNA vector expresses P19, a suppressor of gene silencing, near the left border, and a human β1,4-galactosyltransferase (GalT), encoded by the B4GalT1 gene, near the right border.

For comparing non-galactosylated and galactosylated monoclonal antibodies, three or four genes were transiently co-expressed in *N. benthamiana* to produce a non-galactosylated or galactosylated hD9 IgG1, respectively: hD9 heavy chain (HC), hD9 light chain (LC), and P19, a suppressor of gene-silencing (Garabagi et al., 2012a), with or without human β1,4-galactosyltransferase (GalT). The HC and LC genes were co-expressed from the same vector (pPFC0904; FIG. 1A for T-DNA schematic), and either the P19 and GalT genes were co-expressed using a second vector (pPFC1431; FIG. 1B) or the P19 expressed using a second vector (pPFC0811; FIG. 10).

Figure 2:
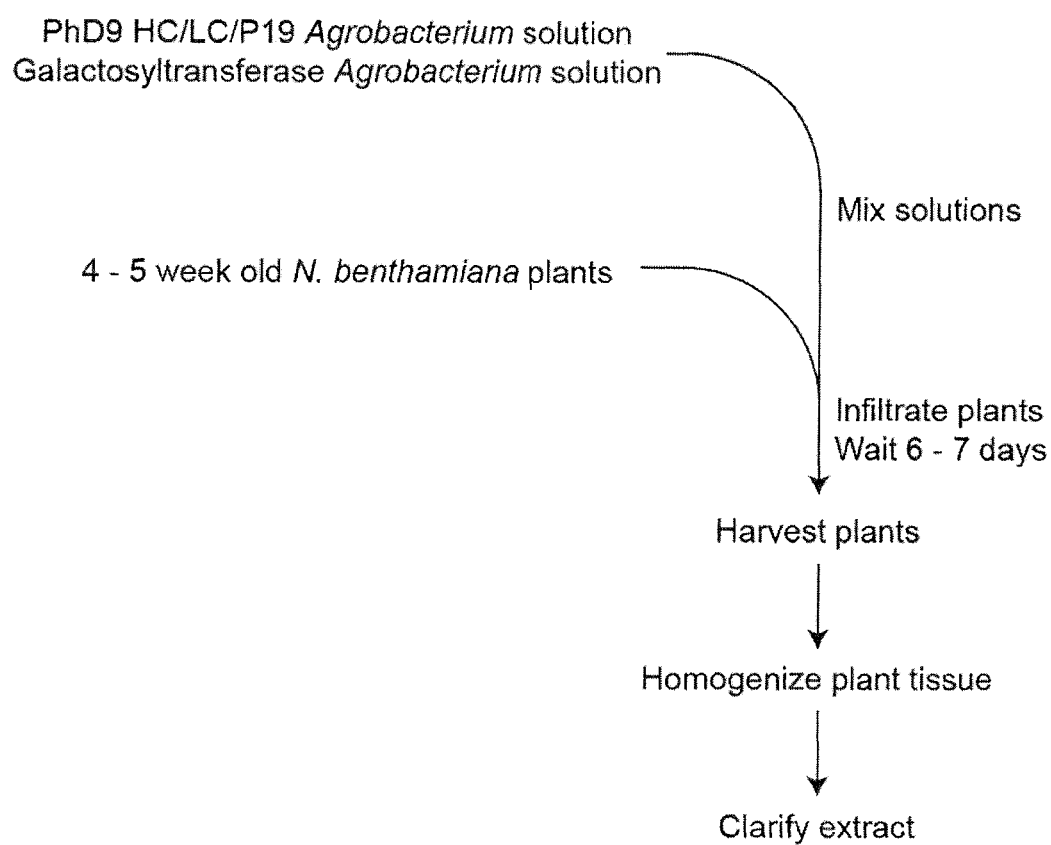
FIG. 2 shows the vivoXPRESS® PhD9 upstream workflow.

Expression levels of hD9 mAbs produced by T-DNA vectors expressing the PhD9 light chain (LC) and PhD9 heavy chain (HC) in divergent directions or in the some direction were compared. FIG. 1A shows one T-DNA vector expresses the PhD9 light chain (LC) and PhD9 heavy chain (HC) in divergent directions. FIG. 1D shows one T-DNA vector expresses the PhD9 light chain (LC) and PhD9 heavy chain (HC) in the same direction.
C. *A. tumefaciens* Expansion and *N. benthamiana* Infiltration FIG. 2 provides a visual representation of the upstream process. Two *Agrobacterium tumefaciens* solutions are expanded overnight; the first expresses the PhD9 T-DNA vector, and the second expresses the P19/GalT T-DNA vector. Those two solutions are mixed and used to vacuum infiltrate four to five weeks old vivoXPRESS® *N. benthamiana* plants that are scalable and engineered to produce antibodies with humanized glycosylation profile. The infiltrated plants are allowed to mature for seven days prior to tissue harvest.

Figure 3:
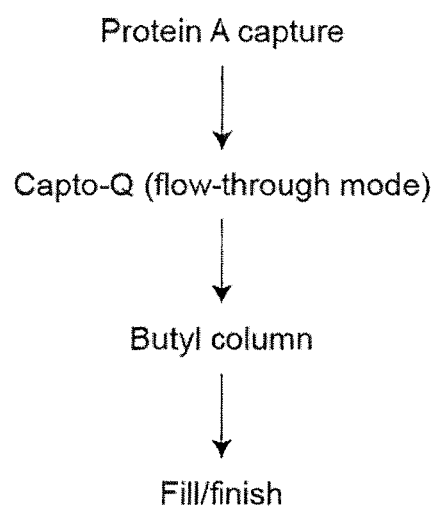
FIG. 3 shows the PhD9 downstream workflow. Aerial plant tissue is harvested seven days post-infiltration and homogenized with buffer.

In particular, transient expression was performed using the homozygous transgenic *N. benthamiana* host line dFX. The dFX line has suppressed expression of two plant-specific glycosyltransferases, α1,3-fucosyltransferase and β1,2-xylosyltransferase (see Strasser et al., 2008). dFX plants produce proteins with detectable levels of xylose and fucose. In another embodiment, *N. benthamiana* host line KDFX is used. The KDFX line has suppressed expression of two plant-specific glycosyltransferases, α1,3-fucosyltransferase and β1,2-xylosyltransferase, resulting in negligible plant-specific glycans. Briefly, *A. tumefaciens* containing either pPFC0904 or pPFC1431 was grown to exponential phase in LB-Miller broth with rifampicin and carbenicillin (50 μg/mL each). *Agrobacteria* cultures were diluted to an $OD_{600}$ of 0.2, per vector/strain, in infiltration buffer (10 mM MES, pH 5.5, 10 mM $MgSO_4$). The foliar areas of the plants were submerged in the *Agrobacteria* solution and exposed to a vacuum for ca. two minutes before slowly returning the chamber to atmospheric pressure. Plants were returned to the greenhouse for six to seven days, after which all aerial tissue was collected for processing.
D. Preparation of a Clarified PhD9 Protein Extract Aerial plant tissue was roughly homogenized in extraction buffer (50 mM phosphate, pH 7.4, 1 M NaCl, 10 mM EDTA, 40 mM ascorbic acid; 1:3 w/v) using a blender, and then finely homogenized using a Polytron. The homogenate was filtered with Miracloth and pH adjusted to 7.4. A filter aid was added to the homogenate, which was then filtered using a 0.45 micron filter press.
E. Protein A Capture FIG. 3 provides a visual representation of the downstream process. Homogenate is clarified through several stages to remove gradually smaller particulate matter. Clarified extract is applied to a Protein A column. For example, the clarified homogenate was applied to MabSelect® affinity column, which is a Protein A chromatography resin, as the first chromatography step to capture PhD9. A 2.5-minute residence time was targeted. The column was washed with 50 mM phosphate, pH 7.4, 1 M NaCl, until the UV trace reached baseline. The bound protein was eluted with 100 mM acetate, pH 3.0, 200 mM arginine, over 2-3 column volumes. The pH of the eluate was adjusted to pH 7.0 immediately with 1 M Tris, pH 8.0. The neutralized Protein A MabSelect® eluate was then dialyzed against 20 mM Tris, pH 7.0 overnight at room temperature in dialysis tubing with a molecular weight cut off of 12-14 kDa.

F. Capto-Q in Flow-Through Mode

The dialyzed Protein A eluate was loaded onto the Capto-Q column with a 10 minutes residence time and the flow through was collected. The column was washed with 5 column volumes of equilibration buffer (20 mM Tris, pH 7.0) and the flow-through fraction was collected until the UV trace reached baseline. The Capto-Q flow-through is then applied to a Butyl HP resin column.

G. Butyl Sepharose Polishing

Fourteen different resins were evaluated, using multiple buffer conditions. Butyl HP resin was found to be optimal under the conditions described here to achieve the desired level of polishing and purity for the PhD9 final product. The conductivity of the Capto-Q flow through was adjusted to approximately 75 mS/cm with 3 M ammonium sulphate solution. The protein solution was loaded onto the Butyl column at a flow-rate of 5-10 mL per minute. The column was washed with 2 column volumes of 20 mM Tris, pH 7.0, 500 mM ammonium sulphate. The bound antibody was eluted using a linear gradient against the elution buffer (20 mM Tris, pH 7.0, 150 mM NaSCN, 15 mM NaCl, 10% glycerol) up to 75% in 4 column volumes. The gradient was kept at 75% elution buffer for additional 2-3 column volumes to collect the peak containing the polished PhD9. The fraction containing the polished PhD9 was dialyzed against 20 mM histidine buffer, pH 6.0.

H. Formulation, Finishing and Analysis

The butyl eluate is then fill-finished. Concentrated PhD9 was formulated by adding 1/10 of its volume of 10 times ultra-filtrated concentrated excipient (200 mM histidine, pH 6.0, 500 mM trehalose, 0.1% polysorbate 80). The formulated PhD9 was filtered (0.2 µm) and aliquoted into 50 mL vials (Type I borosilicate) each containing 50 mg of PhD9 product. PhD9 was lyophilized at 5-10 µmHg for approximately 48 hours. Lyophilized PhD9 final product was reconstituted, aliquoted and endotoxin levels were evaluated using the limulus amebocyte lysate (LAL) assay.

Standard SDS-PAGE analysis was used to compare the reconstituted formulated product to PhD9-2015 (W7702-145668) and Herceptin® (lot H4538). Briefly, three micrograms of protein were electrophoresed on a 10% gel under reducing and non-reducing conditions then stained with Coomassie Brilliant Blue stain. Additionally, one microgram of protein was electrophoresed on a 10% gel under reducing and non-reducing conditions then transferred to PVDF membrane for Western blotting. Membranes were blocked overnight with 3% skim milk and probed with one of three treatments: 1) a mixture of anti-human γ-specific IgG-alkaline phosphatase (AP) and anti-human κ-specific IgG-AP, 2) anti-human γ-specific IgG-AP, or 3) anti-human κ-specific IgG-AP.

Figure 4:
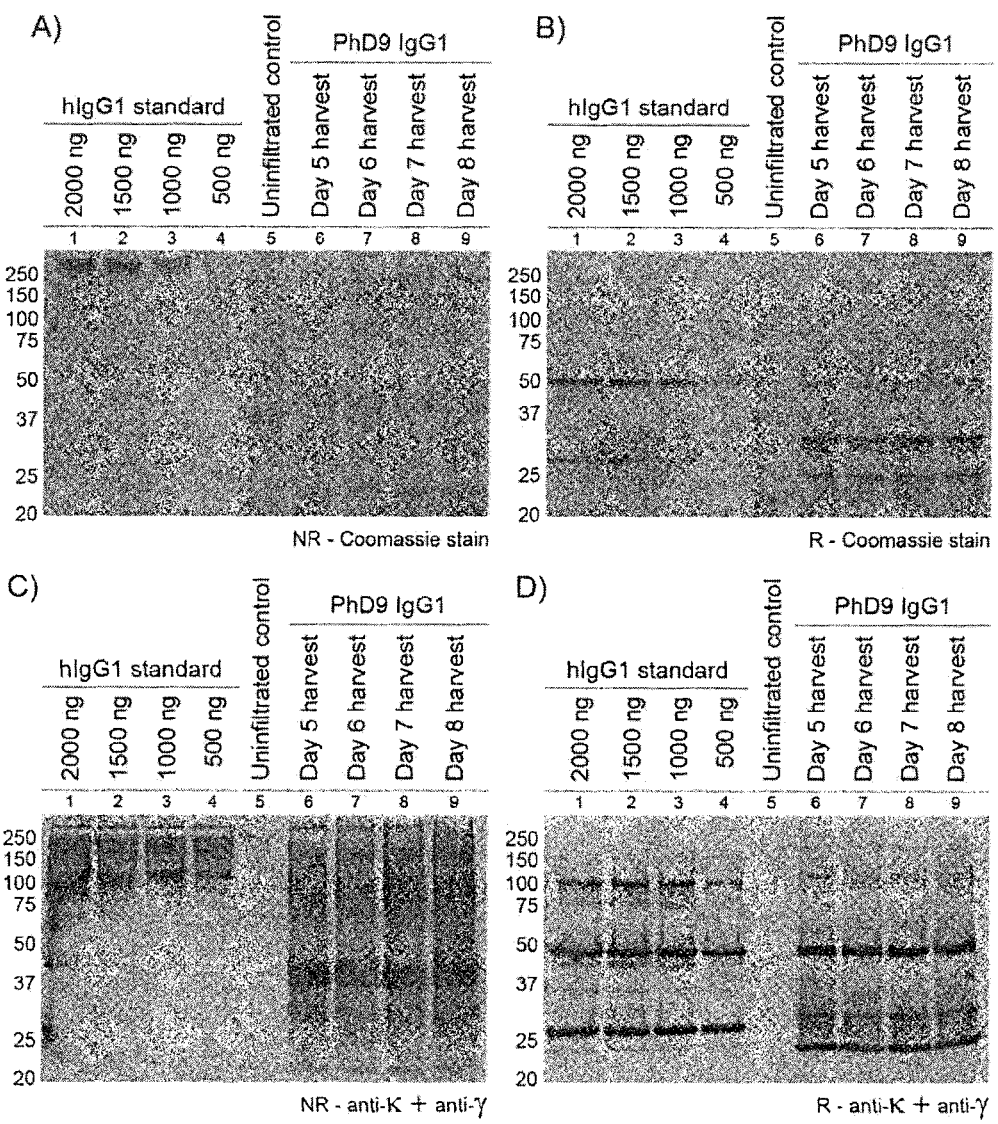
FIG. 4 shows a PhD9 SDS-PAGE analysis from total soluble protein as set out in Example 1. (A) shows non-reducing SDS-PAGE stained with Coomassie Brilliant Blue, (B) shows reducing SDS-PAGE stained with Coomassie Brilliant Blue, (C) shows non-reducing SDS-PAGE transferred to PVDF and probed with anti-human IgG1 κ and γ chain antibodies, visualized with an alkaline phosphatase reaction and (D) shows reducing SDS-PAGE transferred to PVDF and probed with anti-human IgG1 κ and γ chain antibodies, visualized with an alkaline phosphatase reaction.

For example, total soluble protein (TSP) from plants infiltrated with PhD9 and GalT vectors was prepared according to methods above (with additional harvests on days 5, 6, and 9), and resolved by SDS-PAGE. Samples on each panel are accompanied by 500-2000 ng of a human IgG1 standard and an uninfiltrated control. FIG. 4A shows non-reducing SDS-PAGE stained with Coomassie Brilliant Blue. FIG. 4B shows reducing SDS-PAGE stained with Coomassie Brilliant Blue. FIG. 4C shows non-reducing SDS-PAGE transferred to PVDF and probed with anti-human IgG1 κ and γ chain antibodies, visualized with an alkaline phosphatase reaction. FIG. 4D shows reducing SDS-PAGE transferred to PVDF and probed with anti-human IgG1 κ and γ chain antibodies, visualized with an alkaline phosphatase reaction.

Figure 5:
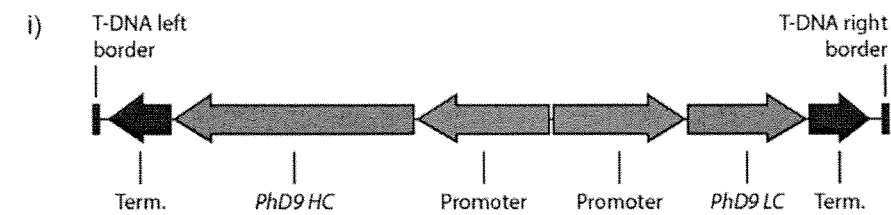
FIG. 5 shows an analysis of PhD9 gene orientation as set out in Example 1. (A) shows a schematic representation of the T-DNA region for the PhD9 vector (pPFC0904) with divergent transcription of the heavy and light chain genes, and the corresponding size exclusion chromatogram of the Protein A eluate. (B) shows a schematic representation of the T-DNA region for the PhD9 vector with the PhD9 heavy chain and light chain genes in the same orientation (pPFC0901), and the corresponding size exclusion chromatogram of the Protein A eluate. (C) shows an analysis of the expression levels in the total soluble protein extracts using BLItz Protein A biosensors. Error bars represent the standard deviation of four biological replicates.
Figure 5:
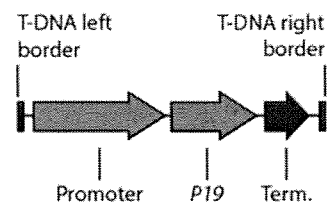
Figure 5:
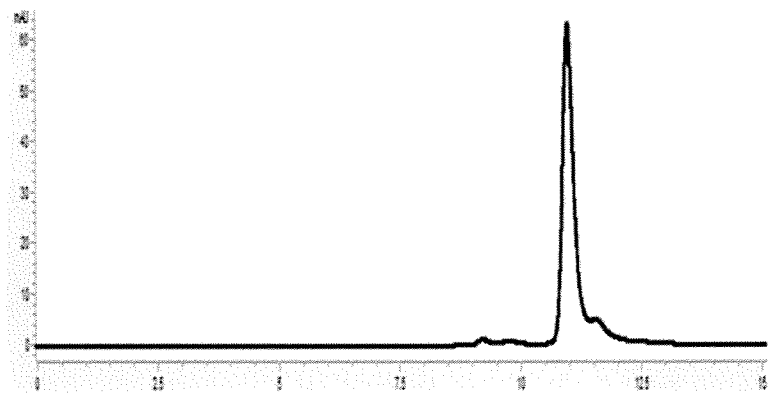
Figure 5:
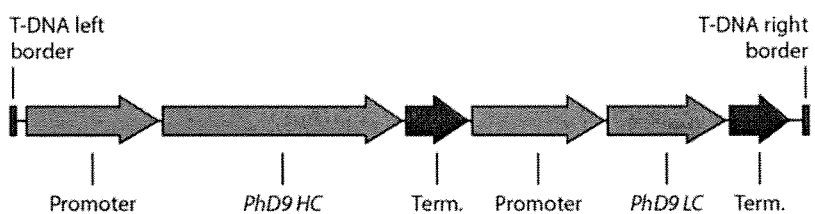
Figure 5:
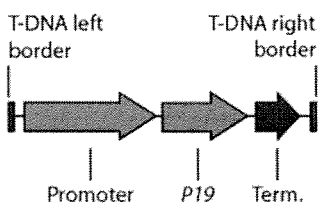
Figure 5:
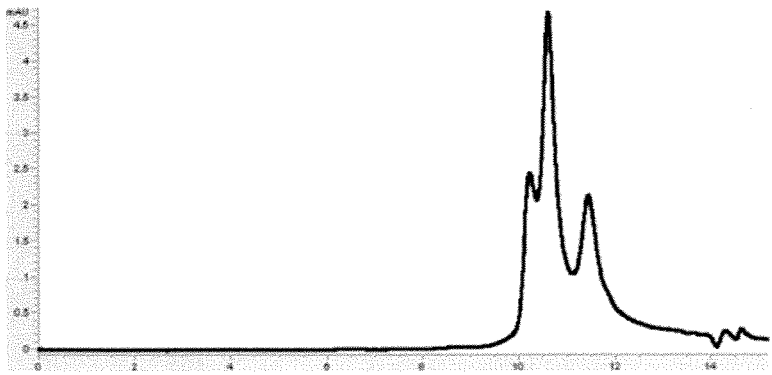

FIG. 5 shows protein A eluate profiles of proteins purified from N. benthamiana plants infiltrated with Agrobacteria containing two different versions of the PhD9 vectors, harvested 6 days post infiltration and processed to purify the PhD9 using Protein A. FIG. 5A shows a schematic representation of the T-DNA region for the PhD9 vector (pPFC0904) with divergent transcription of the heavy and light chain genes, and the corresponding size exclusion chromatogram of the Protein A eluate. FIG. 5B shows a schematic representation of the T-DNA region for the PhD9 vector with the PhD9 heavy chain and light chain genes in the same orientation (pPFC0901), and the corresponding size exclusion chromatogram of the Protein A eluate. FIG. 5C shows an analysis of the expression levels in the total soluble protein extracts using BLItz Protein A biosensors. Error bars represent the standard deviation of four biological replicates.

Figure 6:
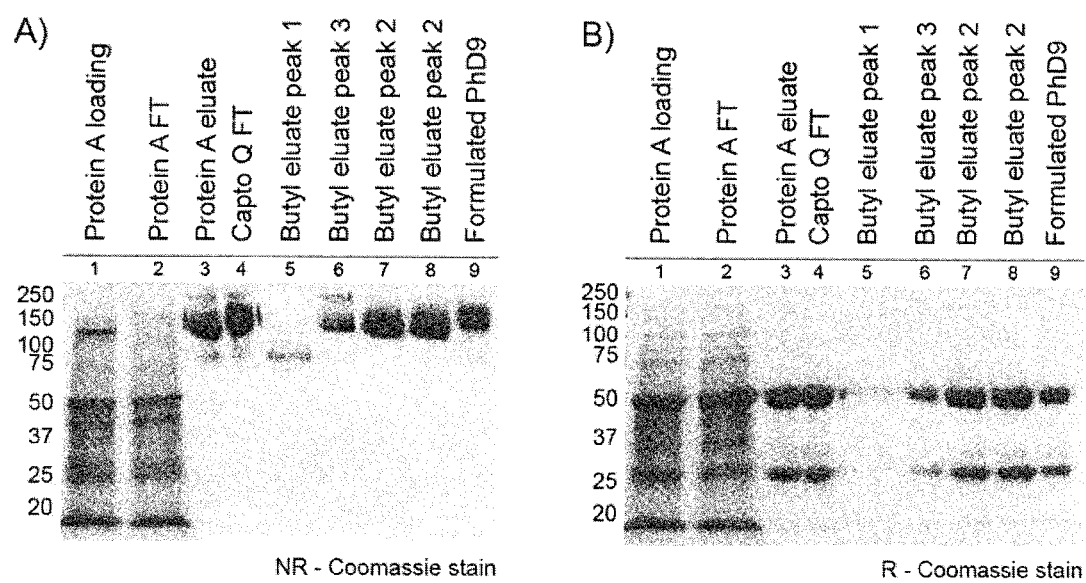
FIG. 6 shows an analysis of PhD9 purification stages and fractions as set out in Example 1. (A) to (F) show the butyl eluate was collected into three fractions for analysis (lanes 5 to 8). Formulated PhD9 was also examined for comparison (lane 9). Samples were resolved by SDS-PAGE. (A) shows non-reducing SDS-PAGE stained with Coomassie Brilliant Blue. (B) shows reducing SDS-PAGE stained with Coomassie Brilliant Blue. (C) shows non-reducing SDS-PAGE transferred to PVDF and probed with anti-human IgG1 γ chain antibody, visualized with an alkaline phosphatase reaction. (D) shows non-reducing SDS-PAGE transferred to PVDF and probed with anti-human IgG1 κ chain antibody, visualized with an alkaline phosphatase reaction. (E) shows reducing SDS-PAGE transferred to PVDF and probed with anti-human IgG1 γ chain antibody, visualized with an alkaline phosphatase reaction. (F) shows reducing SDS-PAGE transferred to PVDF and probed with anti-human IgG1 κ chain antibody, visualized with an alkaline phosphatase reaction. (G) shows Protein A eluate, Capto-Q flow through (FT), and butyl eluate PhD9 purification stages were analyzed by size exclusion chromatography. (H) shows formulated PhD9 analyzed by capillary electrophoresis SDS-PAGE under reducing (top chromatogram) and non-reducing (bottom chromatogram) conditions. (I) shows formulated PhD9 analyzed by 2D SDS-PAGE and Coomassie Blue staining. (J) shows formulated PhD9 analyzed by 2D SDS-PAGE, probed with anti-Human IgG antibody.

PhD9-expressing N. benthamiana tissue was used to prepare clarified extract according to the flow chart in FIG. 2. Samples were collected from each purification stage shown in FIG. 3. FIGS. 6A-F shows the butyl eluate was collected into three fractions for analysis (lanes 5 to 8). Formulated PhD9 was also examined for comparison (lane 9). Samples were resolved by SDS-PAGE. FIG. 6A shows non-reducing SDS-PAGE stained with Coomassie Brilliant Blue. FIG. 6B shows reducing SDS-PAGE stained with Coomassie Brilliant Blue. FIG. 6C shows non-reducing SDS-PAGE transferred to PVDF and probed with anti-human IgG1 γ chain antibody, visualized with an alkaline phosphatase reaction. FIG. 6D shows non-reducing SDS-PAGE transferred to PVDF and probed with anti-human IgG1 κ chain antibody, visualized with an alkaline phosphatase reaction. FIG. 6E shows reducing SDS-PAGE transferred to PVDF and probed with anti-human IgG1 γ chain antibody, visualized with an alkaline phosphatase reaction. FIG. 6F shows reducing SDS-PAGE transferred to PVDF and probed with anti-human IgG1 κ chain antibody, visualized with an alkaline phosphatase reaction. FIG. 6G shows Protein A eluate, Capto-Q flow through (FT), and butyl eluate PhD9 purification stages were analyzed by size exclusion chromatography. FIG. 6H shows formulated PhD9 analyzed by capillary electrophoresis-SDS (CE-SDS) under reducing (top chromatogram) and non-reducing (bottom chromatogram) conditions. FIG. 6I shows formulated PhD9 analyzed by 2D SDS-PAGE and Coomassie Blue staining. FIG. 6J shows formulated PhD9 analyzed by 2D SDS-PAGE, probed with anti-human IgG antibody.

Figure 7:
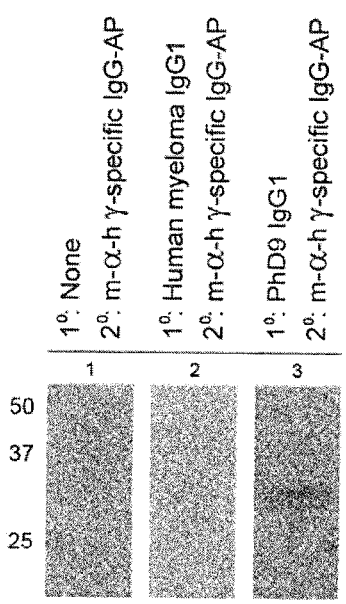
FIG. 7 shows that PhD9 binds to ricin B chain in vitro. (A) shows one microgram of ricin B chain resolved by SDS-PAGE and transferred to PVDF. The membrane was probed with only secondary antibody (lane 1), human myeloma IgG1 primary and mouse α-human secondary antibody (lane 2), or PhD9 primary and mouse α-human secondary antibody (lane 3). In (B), ricin B chain was used to coat a microwell plate, followed by probing with PhD9 (0.0-10.0 μg/mL) and analysis by ELISA.
Figure 7:
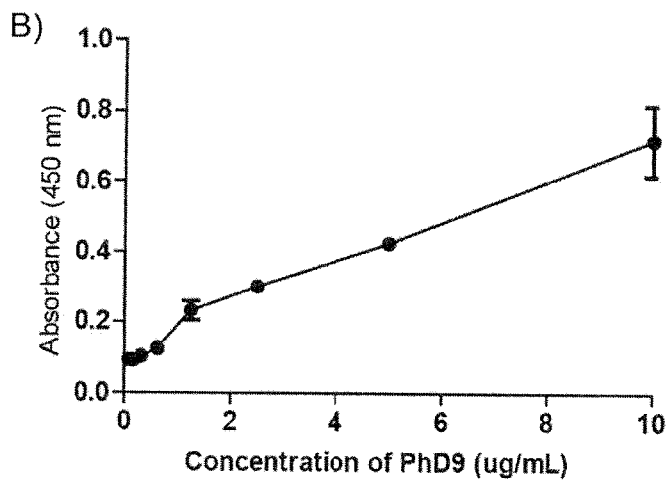

In another analysis, PhD9-expressing N. benthamiana tissue was used to prepare clarified extract according to the flow chart in FIG. 2. PhD9 was purified according to FIG. 3. FIG. 7A shows one microgram of ricin B chain was resolved by SDS-PAGE and transferred to PVDF. The membrane was probed with only secondary antibody (lane 1), human myeloma IgG1 primary and mouse α-human secondary antibody (lane 2), or PhD9 primary and mouse α-human secondary antibody (lane 3). FIG. 7B shows ricin B chain was used to coat a microwell plate, followed by probing with PhD9 (0.0-10.0 µg/mL) and analysis by ELISA.

I. Size Exclusion Chromatography Analysis

Size-exclusion chromatography was performed using a Yarra 3u SEC-3000 column connected to an Agilent 1100 Series HPLC. Each sample (minimum 5 µL—concentration dependent) was injected into the HPLC using a flow rate of 0.75 mL/minute and separated based on size until the UV trace reached baseline. Agilent OpenLAB, Chemstation Edition software was used to integrate the area under the curve.

J. In Vitro Neutralization Assay

A Vero cell toxicity neutralization assay with Alamar Blue as an indicator was performed in 96-well plates. Ricin was incubated with a serial dilution of PhD9, hD9, or an unrelated antibody (control) for 2 hours at 37° C. Vero cells were added into the ricin antibody mixture. After incubation at 37° C., 5% $CO_2$ for 2 days, Alamar Blue was added and incubated for 6-7 hours. On a plate reader, the plate was read at an absorbance of 570 nm with 600 nm as a reference.

Figure 8:
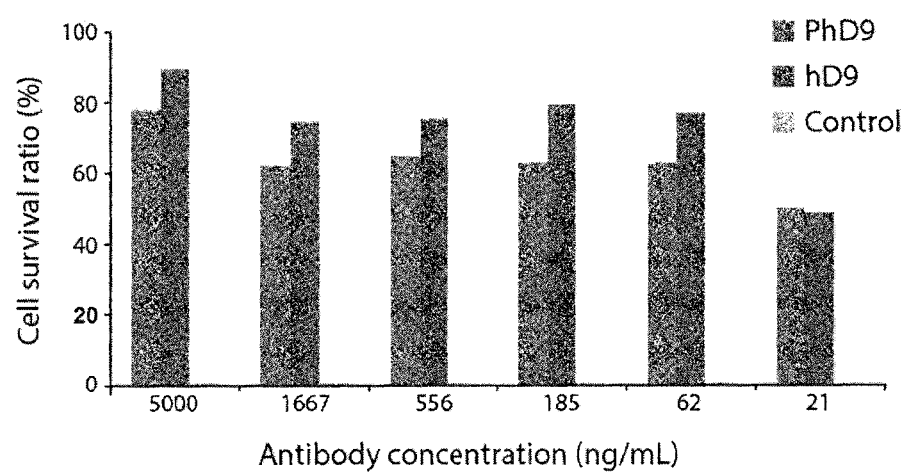
FIG. 8 shows a Vero cell in vitro survival assay as set out in Example 1.

For example, FIG. 8 shows a Vero cell toxicity neutralization assay with Alamar Blue as an indicator was performed in 96-well plates. Ricin was incubated with a serial dilution of PhD9, hD9, or an unrelated antibody (control) for 2 hours at 37° C. Vero cells were added into the ricin antibody mixture. After incubation at 37° C., 5% $CO_2$ for 2 days, Alamar Blue was added and incubated for 6-7 hours. On a plate reader, the plate was read at an absorbance of 570 nm with 600 nm as a reference.

K. In Vivo Protection Assay

Groups of 5-8 Balb/c female mice (4-6 weeks old) were intraperitoneally challenged with $5 \times LD_{50}$ ricin. Five µg per mouse of PhD9, hD9, or an unrelated antibody (control) was intraperitoneally administered to mice at 4 or 6 hours post-ricin challenge. The mice were observed for morbidity and mortality over two weeks.

Results and Discussion

Gene Orientation Analysis of PhD9 Expression

N. benthamiana plants were infiltrated with A. tumefaciens clones containing two versions of the expression vectors for the anti-ricin hD9 heavy chain, light chain and P19 (suppressor of gene-silencing). Version one of the expression vector contained the PhD9 heavy chain and light chain genes in divergent directions (FIG. 5A), whereas version two contained the genes in the same direction (FIG. 5B). Divergent directions of the PhD9 heavy chain and light chain genes led to a two-fold increase in PhD9 expression levels when evaluated in total soluble protein extracts (FIG. 5C). Additionally, the percentage of intact IgG1 following Protein A purification increased from ca. 50% to ca. 80% according to area under the curve analysis of size exclusion chromatography (FIG. 5B and FIG. 5A, respectively).

Time-Course Analysis of PhD9 Expression

N. benthamiana plants were infiltrated, as described herein, with A. tumefaciens clones carrying the genes for the anti-ricin hD9 antibody heavy chain, light chain, P19 (suppressor of gene-silencing) and a human β1,4-galactosyltransferase. Plant tissue was harvested on days 5, 6, 7, and 8 and subjected to the clarification procedure, as described. The clarified extract was resolved by SDS-PAGE (FIG. 4) under reducing or non-reducing conditions, and stained with Coomassie Brilliant Blue or transferred to PVDF and probed with anti-κ and anti-γ primary antibodies. These data demonstrate robust PhD9 antibody expression over the queried days.

Purification and Analysis of PhD9

As described, the purification process for PhD9 began with a Protein A affinity chromatography step, followed by ion exchange chromatography (IEC) to remove endotoxin, host cell proteins and nucleic acids. The final polishing step, hydrophobic interaction chromatography (HIC), removed degraded and aggregated PhD9. Eluted PhD9 was collected in fractions to isolate the intact tetrameric PhD9 product.

Representative samples from major stages in the PhD9 purification process were resolved by SDS-PAGE (under both reducing and non-reducing conditions) and visualized by Coomassie Brilliant Blue staining (FIGS. 6A and B) or by SDS-PAGE followed by transfer to PVDF and probing with anti-κ and anti-γ (FIGS. 6C-F). PhD9 samples from the Protein A eluate, Capto-Q flow through, and Butyl sepharose eluate fractions were analyzed by size exclusion chromatography (FIG. 6G). Analysis by SEC of the Butyl eluate demonstrates a high degree of purity (>94% intact IgG1). Reduced and non-reduced reconstituted PhD9 was analyzed by capillary electrophoresis-SDS (CE-SDS; FIG. 6H). The reducing CE-SDS chromatogram showed a single peak corresponding to the light chain and two peaks corresponding to two forms of the heavy chain, aglycosylated and glycosylated. The non-reducing CE-SDS chromatogram indicated there were three different IgG1 forms as a result of the two forms of the heavy chain: aglycosylated IgG1, partially glycosylated IgG1, and glycosylated IgG1. Intact IgG1 comprised >94% of the PhD9 reconstituted sample. Reconstituted PhD9 was also analyzed by two dimensional SDS-PAGE (FIG. 6I) and Western blotting (FIG. 6J) to detect host cell protein impurities. Western blot films and the Coomassie stained gel were scanned with a laser densitometer and cross-referenced to each other to detect host cell protein impurities. The anti-human IgG antibody detected 99.9% of the Coomassie stain density for the protein in the PhD9 sample. Therefore, there were less than 0.1% host cell protein impurities in the PhD9 product.

PhD9 Protects From Ricin Both In Vitro and In Vivo

Vero cells were incubated with ricin and hD9 (HEK produced), PhD9, or control antibody (FIG. 8). Both hD9 and PhD9 exerted a similar protective effect down to 20 ng antibody per mL growth medium.

Figure 9:
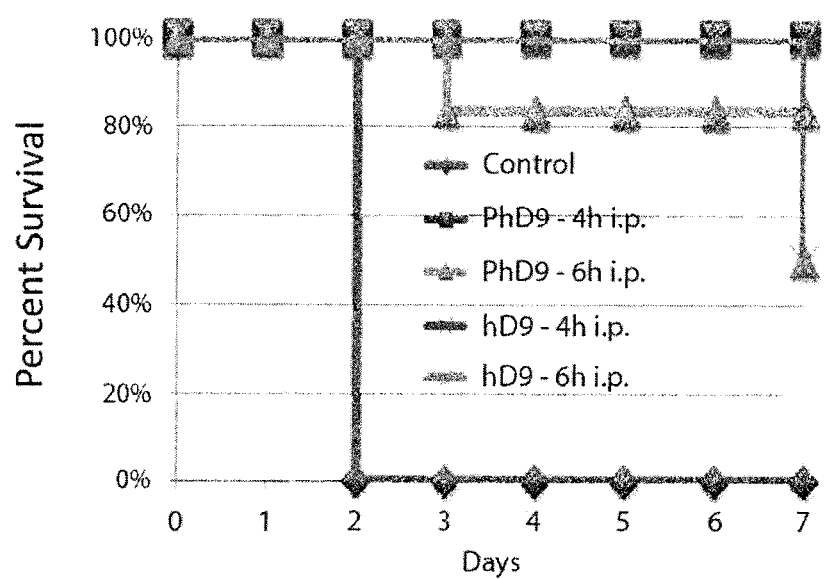
FIG. 9 shows a murine ricin in vivo challenge and PhD9 rescue as set out in Example 1.

A control antibody, hD9, or PhD9 was administered to Balb/C mice either 4 hours or 6 hours after a $5 \times LD_{50}$ ricin challenge (FIG. 9). Two days post-administration, all mice receiving the control antibody had succumbed to the ricin challenge. The groups that received hD9 and PhD9 four hours after ricin challenge had a 100% survival rate, and those that received hD9 and PhD9 six hours after challenge had a 50% survival rate.

Genetically Modified Plants Offer an Alternative

Pharmaceutical industry or government requires a scalable process that is amenable to GMP manufacturing for the production of anti-ricin antibodies.

Herein, the inventors have described how to apply a plant-based scalable system to express the hD9 anti-ricin antibody, and the three-stage chromatography method required to isolate the tetrameric IgG from clarified extract. The final product described here was a >94% pure, sterile PhD9 antibody with a humanized glycosylation profile that contains ≤5% plant-specific fucose and xylose, and with ≤0.1 endotoxin units per milligram of antibody.

This shows that a plant-expression and purification system can produce a mAb with similar in vitro and in vivo bioactivities to one produced by mammalian cells, supporting plant expression systems as effective alternatives to mammalian cell systems for the production of mAbs for disease treatment.

While the present disclosure has been described with reference to what are presently considered to be the preferred example, it is to be understood that the disclosure is not limited to the disclosed example. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| | Sequences |
|---|---|
| SEQ ID NO: 1 nucleic acid coding sequence of the heavy chain variable region of PhD9 | CAAGTCCAGTTGGTTCAAAGCGGAGCTGAAGTT AAGAAACCTGGAGCTTCTGTAAAAGTGTCTTGTA AAGCTAGTGGATATACTTTTACTGAACACATCAT TAATTGGGTGAGGCAAGCTCCAGGTCAAAACTT GGAATGGATGGGACTTATTAATCCTAATAGCGG AGGCACTAACTACAACCAAAAGTTCAAGGATCGT GTGACTATGACTACCGATACTTCTACTTCCACTG CCTATATGGAGTTGCTCAGCCTTCGTTCCGATGA CACAGCAGTTTATTACTGTGCAAGGTTGAGATAT GATGCTGCCTACTGGGGTCAGGGGACAACTGTT ACTGTTAGTTCT |
| SEQ ID NO: 2 nucleic acid coding sequence of the CDR H1 of PhD9 | GAACACATCATTAAT |
| SEQ ID NO: 3 nucleic acid coding sequence of the CDR H2 of PhD9 | CTTATTAATCCTAATAGCGGAGGCACTAACTACA ACCAAAAGTTCAAGGAT |
| SEQ ID NO: 4 nucleic acid coding sequence of the CDR H3 of PhD9 | TTGAGATATGATGCTGCCTAC |
| SEQ ID NO: 5 amino acid sequence of the heavy chain variable region of PhD9 | QVQLVQSGAEVKKPGASVKVSCKASGYTFTEHIIN WVRQAPGQNLEWMGLINPNSGGTNYNQKFKDRV TMTTDTSTSTAYMELLSLRSDDTAVYYCARLRYDA AYWGQGTTVTVSS |
| SEQ ID NO: 6 amino acid sequence of the CDR H1 of PhD9 | EHIIN |
| SEQ ID NO: 7 amino acid sequence of the CDR H2 of PhD9 | LINPNSGGTNYNQKFKD |
| SEQ ID NO: 8 amino acid sequence of the CDR H3 of PhD9 | LRYDAAY |
| SEQ ID NO: 9 nucleic acid coding sequence of the light chain variable region of PhD9 | GATATCCAAATGACTCAGTCACCATCATCTTTGA GTGCTTCAGTGGGTGACCGTGTCACCATTACAT GTAAGGCCAGCCAGGATGTGACAGCCGCTGTC GCCTGGTATCAGCAAAAGCCAGGAAAAGCACCT AAATTGCTTATTTACTCTGCTAGCTACAGGTATA CAGGTGTTCCTAGTAGATTTAGTGGATCAGGATC TGGGACTGATTTCACACTGACAATAAGCTCTCTT CAACCAGAAGATTTCGCAACTTATTACTGCCAAC AGTACTATAACACTCCATTGACTTTTGGGGGTGG CACTAAGGTTGAGATCAAG |
| SEQ ID NO: 10 nucleic acid coding sequence of the CDR L1 of PhD9 | AAGGCCAGCCAGGATGTGACAGCCGCTGTCGC C |

TABLE 1-continued

Sequences

SEQ ID NO: 11 nucleic acid coding sequence of the CDR L2 of PhD9

TCTGCTAGCTACAGGTATACA

SEQ ID NO: 12 nucleic acid coding sequence of the CDR L3 of PhD9

CAACAGTACTATAACACTCCATTGACT

SEQ ID NO: 13 amino acid sequence of the light chain variable region of PhD9

DIQMTQSPSSLSASVGDRVTITCKASQDVTAAVAW
YQQKPGKAPKLLIYSASYRYTGVPSRFSGSGSGT
DFTLTISSLQPEDFATYYCQQYYNTPLTFGGGTKV
EIK

SEQ ID NO: 14 amino acid sequence of the CDR L1 of PhD9

KASQDVTAAVA

SEQ ID NO: 15 amino acid sequence of the CDR L2 of PhD9

SASYRYT

SEQ ID NO: 16 amino acid sequence of the CDR L3 of PhD9

QQYYNTPLT

SEQ ID NO: 17 nucleic acid sequence of p19 suppressor of gene-silencing protein

ATGGAAAGGGCTATTCAGGGAAATGATGCTAGA
GAGCAGGCTAATTCTGAAAGATGGGATGGTGGA
TCTGGTGGAACTACTTCTCCATTCAAGCTTCCAG
ATGAGTCTCCATCTTGGACTGAGTGGAGGCTTC
ATAACGATGAGACTAACTCCAATCAGGATAACCC
ACTCGGATTCAAAGAATCTTGGGGATTCGGAAA
GGTTGTGTTCAAGCGTTACCTTAGGTATGATAGG
ACTGAGGCTTCACTTCATAGGGTTCTCGGATCTT
GGACTGGTGATTCTGTTAACTACGCTGCTTCTCG
TTTTTTTGGATTCGATCAGATCGGATGCACTTAC
TCTATTAGGTTCAGGGGAGTGTCTATTACTGTTT
CTGGTGGATCTAGGACTCTTCAACACCTTTGCG
AGATGGCTATTAGGTCTAAGCAAGAGCTTCTTCA
GCTTGCTCCAATTGAGGTTGAGTCTAACGTTTCA
AGAGGATGTCCAGAAGGTACTGAGACTTTCGAG
AAAGAATCCGAG

SEQ ID NO: 18 amino acid sequence of p19 suppressor of gene-silencing protein

MERAIQGNDAREQANSERWDGGSGGTTSPFKLP
DESPSWTEWRLHNDETNSNQDNPLGFKESWGFG
KVVFKRYLRYDRTEASLHRVLGSWTGDSVNYAAS
RFFGFDQIGCTYSIRFRGVSITVSGGSRTLQHLCE
MAIRSKQELLQLAPIEVESNVSRGCPEGTETFEKE
SE

SEQ ID NO: 19 nucleic acid coding sequence of human β1,4-galactosyltransferase (B4GalT1)

ATGATTCACACGAACCTGAAGAAGAAGTTCAGC
CTCTTCATCCTGGTTTTCCTGCTCTTCGCGGTAA
TCTGCGTTTGGAAGAAGGGTTCTGACTACGAAG
CCCTCACCCTCCAGGCGAAGGAATTCCAGATGC
CGAAGTCTCAGGAGAAGGTTGCCGCAGCCATCG
GTCAGTCCTCTGGTGAACTCCGTACCGGTGGTG
CTCGTCCTCCACCGCCGCTGGGTGCATCTAGCC
AGCCGCGTCCGGGTGGCGACAGCTCTCCGGTT
GTGGATTCTGGCCCAGGTCCAGCTTCTAACCTG
ACGTCTGTTCCGGTTCCACATACCACCGCGCTC
AGCCTGCCGGCGTGCCCGAAGAATCTCCGCT
GCTGGTAGGCCCTATGCTCATCGAATTCAACAT
GCCGGTAGACCTGGAACTCGTTGCGAAGCAGAA
CCCGAACGTAAAGATGGGTGGTCGCTACGCCCC
TCGTGATTGCGTTTCCCCGCACAAGGTGGCCAT
CATCATTCCTTTCCGTAACCGTCAAGAGCACCTG
AAATACTGGCTGTACTACCTGCACCCGGTTCTG
CAGCGTCAGCAGCTCGACTACGGTATCTACGTT
ATCAACCAGGCGGGTGACACCATCTTTAACCGC
GCTAAACTGCTGAACGTGGGTTTCCAGGAGGCG
CTCAAGGATTACGACTACACCTGCTTCGTTTTCT
CTGACGTTGACCTGATCCCGATGAATGATCACA
ACGCCTACCGTTGCTTTTCTCAACCACGTCACAT
CTCTGTTGCGATGGACAAATTCGGTTTCTCTCTC
CCGTATGTACAGTACTTCGGTGGCGTGTCTGCC
CTCTCTAAGCAGCAATTCCTGACGATCAACGGTT

TABLE 1-continued

| | Sequences |
|---|---|
| | TCCCGAACAATTACTGGGGTTGGGGTGGTGAAG ACGATGATATCTTCAACCGCCTCGTATTCCGCG GTATGTCTATCAGCCGTCCGAATGCGGTCGTGG GCCGCTGCCGTATGATCCGTCACAGCCGTGACA AGAAGAACGAGCCGAACCCGCAGCGCTTTGACC GTATCGCGCACACCAAAGAAACTATGCTGTCTG ACGGCCTGAACTCTCTCACGTACCAAGTTCTCG ACGTACAGCGTTACCCGCTGTATACCCAGATCA CCGTCGACATCGGTACCCCGTCT |
| SEQ ID NO: 20 amino acid sequence of human β1,4-galactosyltransferase | MIHTNLKKKFSLFILVFLLFAVICVWKKGSDYEALTL QAKEFQMPKSQEKVAAAIGQSSGELRTGGARPPP PLGASSQPRPGGDSSPVVDSGPGPASNLTSVPVP HTTALSLPACPEESPLLVGPMLIEFNMPVDLELVAK QNPNVKMGGRYAPRDCVSPHKVAIIIPFRNRQEHL KYWLYYLHPVLQRQQLDYGIYVINQAGDTIFNRAK LLNVGFQEALKDYDYTCFVFSDVDLIPMNDHNAYR CFSQPRHISVAMDKFGFSLPYVQYFGGVSALSKQ QFLTINGFPNNYWGWGGEDDDIFNRLVFRGMSIS RPNAVVGRCRMIRHSRDKKNEPNPQRFDRIAHTK ETMLSDGLNSLTYQVLDVQRYPLYTQITVDIGTPS |
| SEQ ID NO: 21 amino acid sequence of *Arabidopsis thaliana* basic chitinase signal peptide | MAKTNLFLFLIFSLLLSLSSA |

REFERENCES

Almquist, K. C., Niu, Y., McLean, M. D., Mena, F. L., Yau, K. Y., Brown, K., Brandle, J. E. and Hall, J. C. (2004) Immunomodulation confers herbicide resistance in plants. *Plant Biotechnol J* 2, 189-197.

Almquist, K. C., McLean, M. D., Niu, Y., Byrne, G., Olea-Popelka, F. C., Murrant, C., Barclay, J. and Hall, J. C. (2006) Expression of an anti-botulinum toxin A neutralizing single-chain Fv recombinant antibody in transgenic tobacco. *Vaccine* 24, 2079-2086.

Altschul, S. F., Gish, W., Miller, W., Myers, E. W. and Lipman, D. J. (1990) Basic local alignment search tool." *Journal of molecular biology* 215, 403-410.

Altschul, S. F., Madden, T. L., Schäffer, A. A., Zhang, J., Zhang, Z., Miller, W. and Lipman, D. J. (1997) Gapped BLAST and PSI-BLAST: a new generation of protein database search programs. *Nucleic acids research* 25, 3389-3402.

Birch, J. R. and Racher, A. J. (2006) Antibody production. *Advanced Drug Delivery Reviews* 58, 671-685.

Brodsky, L. I., Ivanov, V. V., Kalaidzidis, Y. L., Leontovich, A. M., Nikolaev, V. K., Feranchuk, S. I. and Drachev, V. A. (1995) GeneBee-NET: internet-based server for analyzing biopolymers structures. *Biochemestry* 60, 923-928.

Broothaerts, W., Mitchell, H. J., Weir, B., Kaines, S., Smith, L. M. A., Yang, W., Mayer, J. E., Roa-Rodriguez, C. and Jefferson, R. A. (2005) Gene transfer to plants by diverse species of bacteria. *Nature* 433, 629-633.

Burnett, J. C., Henchal, E. A., Schmaljohn, A. L. and Bavari, S. (2005) The evolving field of biodefence: therapeutic developments and diagnostics. *Nat Rev Drug Discov* 4, 281-297.

Chen, Q. and Davis, K. R. (2016) The potential of plants as a system for the development and production of human biologics. *F1000Research* 5.

Chung, S. M., Vaidya, M. and Tzfira, T. (2006) Agrobacterium is not alone: gene transfer to plants by viruses and other bacteria. *Trends Plant Sci* 11, 1-4.

CNR National Research Council. SpliceView. WebGene Webpage available on-line at www.itb.cnr.it/sun/webgene/

Colgan, R., Atkinson, C. J., Paul, M., Hassan, S., Drake, P. M., Sexton, A. L., Santa-Cruz, S., James, D., Hamp, K., Gutteridge, C. and Ma, J. K. (2010) Optimisation of contained *Nicotiana tabacum* cultivation for the production of recombinant protein pharmaceuticals. *Transgenic Res* 19, 241-56.

Conley, A. J. (2009) Chapter 4: Recombinant Protein Production in a variety of *Nicotiana* hosts: A comparative analysis. In: Approaches for Enhancing Recombinant Protein Production in Transgenic Plants; PhD Thesis, The School of Graduate and Postdoctoral Studies, The University of Western Ontario, London, Ontario, Canada.

Doan, L. G. (2004) Ricin: mechanism of toxicity, clinical manifestations, and vaccine development. A review. Journal of Toxicology: *Clinical Toxicology* 42, 201-208.

Foxwell, B. M. J., Detre, S. I., Donovan, T. A. and Thorpe, P. E. (1985) The use of anti-ricin antibodies to protect mice intoxicated with ricin. *Toxicology* 34, 79-88.

Gagnon, P. (2012) Technology trends in antibody purification. *Journal of chromatography A* 1221, 57-70.

Garabagi, F., Gilbert, E., Loos, A., McLean, M. D. and Hall, J. C. (2012) Utility of the P19 suppressor of gene-silencing protein for production of therapeutic antibodies in *Nicotiana* expression hosts. *Plant Biotechnol J* 10, 1118-1128. [Garabagi et al., 2012a]

Garabagi, F., McLean, M. D. and Hall, J. C. (2012) Transient and stable expression of antibodies in *Nicotiana* species. *Methods Mol Biol* 907, 389-408. [Garabagi et al., 2012b]

Gardiner-Garden, M. and Frommer, M. (1987) CpG islands in vertebrate genomes. *J Mol Biol* 196, 261-282.

Gavilondo, J. V. and Larrick, J. W. (2000) Antibody engineering at the millennium. *Biotechniques* 29, 128-32, 134-6, 138 passim.

Gelvin, S. B. (2003) *Agrobacterium*-mediated plant transformation: the biology behind the "gene-jockeying" tool. *Microbiol Mol Biol Rev* 67, 16-37.

GeneBee Molecular Biology Server. RNA secondary structure prediction. Available on-line at www.genebee.msu.su/services/rna2_reduced.html Giritch, A., Marillonnet, S., Engler, C., van Eldik, G., Botterman, J., Klimyuk, V. and Gleba, Y. (2006) Rapid high-yield expression of full-size IgG antibodies in plants coinfected with noncompeting viral vectors. *Proc Natl Acad Sci USA* 103, 14701-14706.

Guo, J., Shen, B., Sun, Y., Yu, M. and Hu, M. (2006) A novel neutralizing monoclonal antibody against both ricin toxin A and ricin toxin B, and application of a rapid sandwich enzyme-linked immunosorbent assay. *Hybridoma* 25, 225-229.

Hewetson, J. F., Rivera, V. R, Creasia, D. A., Lemley, P. V., Rippy, M. K. and Poli, M. A. (1993) Protection of mice from inhaled ricin by vaccination with ricin or by passive treatment with heterologous antibody. *Vaccine* 11, 743-746.

Hiatt, A., Cafferkey, R. and Bowdish, K. (1989) Production of antibodies in transgenic plants. *Nature* 342, 76-78.

Horsch, R. B., Fry, J. E., Hoffmann, N. L., Eichholtz, D., Rogers, S. G. and Fraley, R. T. (1985) A simple and general method for transferring genes into plants. *Science* 227, 1229-1231.

Hu, W. G., Yin, J., Chau, D., Negrych, L. M. and Cherwonogrodzky, J. W. (2012). Humanization and characterization of an anti-ricin neutralization monoclonal antibody. *PLoS One* 7, e45595.

Karg, S. R. and Kallio, P. T. (2009) The production of biopharmaceuticals in plant systems. *Biotechnology advances* 27, 879-894.

Karlin, S. and Altschul, S. F. (1990) Methods for assessing the statistical significance of molecular sequence features by using general scoring schemes. *Proceedings of the National Academy of Sciences* 87, 2264-2268.

Karlin, S. and Altschul, S. F. (1993) Applications and statistics for multiple high-scoring segments in molecular sequences. *Proceedings of the National Academy of Sciences* 90, 5873-5877.

Ko, K., Brodzik, R. and Steplewski, Z. (2009) Production of antibodies in plants: approaches and perspectives. *Plant-produced Microbial Vaccines*. Springer Berlin Heidelberg, 55-78.

Kozak, M. (1984) Compilation and analysis of sequences upstream from the translational start site in eukaryotic mRNAs. *Nucleic Acids Res* 12, 857-872.

Lai, H., Engleb, M., Fuchsb, A., Keller, T., Johnson, S., Gorlatovc, S., Diamond, M. S. and Chen, Q. (2010) Monoclonal antibody produced in plants efficiently treats West Nile virus infection in mice. *Proceedings of the National Academy of Sciences USA* 107, 2419-2424.

Lee, L.-Y., Kononov, M. E., Bassuner, B., Frame, B. R., Wang, K. and Gelvin, S. B. (2007) Novel Plant Transformation Vectors Containing the Superpromoter. *Plant Phys* 145, 1294-1300.

Li, Q. and Hunt, A. (1995) A near-stream element in a plant polyadenylation signal consist of more than six nucleotides. *Plant Mol Biol* 28, 927-934.

Ma, J. K., Drossard, J., Lewis, D., Altmann, F., Boyle, J., Christou, P., Cole, T., Dale, P., van Dolleweerd, C. J., Isitt, V., et al. (2015) Regulatory approval and a first-in-human phase I clinical trial of a monoclonal antibody produced in transgenic tobacco plants. *Plant Biotechnol J* 13, 1106-1120.

Makvandi-Nejad, S., McLean, M. D., Hirama, T., Almquist, K. C., Mackenzie, C. R. and Hall, J. C. (2005) Transgenic tobacco plants expressing a dimeric single-chain variable fragment (scfv) antibody against *Salmonella enterica* serotype Paratyphi B. *Transgenic Res* 14, 785-792.

Marillonnet, S., Thoeringer, C., Kandzia, R., Klimyuk, V. and Gleba, Y. (2005). Systemic *Agrobacterium tumefaciens*-mediated transfection of viral replicons for efficient transient expression in plants. *Nat Biotechnol* 23, 718-723.

McLean, M. D., Almquist, K. C., Niu, Y., Kimmel, R., Lai, Z., Schreiber, J. R. and Hall, J. C. (2007) A Human Anti-Pseudomonas aeruginosa Serotype O6ad Immunoglobulin G1 Expressed in Transgenic Tobacco Is Capable of Recruiting Immune System Effector Function In Vitro. *Antimicrob Agents Chemother* 51, 3322-3328.

Miller, D. J., Ravikumar, K., Shen, H., Suh, J. K., Kerwin, S. M. and Robertus, J. D. (2002) Structure-based design and characterization of novel platforms for ricin and shiga toxin inhibition. *J Med Chem* 45, 90-98.

Montanaro, L., Sperti, S. and Stirpe, F. (1973) Inhibition by ricin of protein synthesis in vitro. Ribosomes as the target of the toxin. *Biochem J* 136, 677-683.

Morelle, W., and Michalski, J.-C. (2005) The mass spectrometric analysis of glycoproteins and their glycan structures. *Current Analytical Chemistry* 1, 29-57.

Myers, E. W. and Miller, W. (1988) Optimal alignments in linear space. *Computer applications in the biosciences: CABIOS* 4, 11-17.

Nakamura, Y. (2005) Codon usage database. Available online at www.kazusa.or.jp/codon.

Neal, L. M., O'Hara, J., Brey, R. N. and Mantis, N. J. (2010) A monoclonal immunoglobulin G antibody directed against an immunodominant linear epitope on the ricin A chain confers systemic and mucosal immunity to ricin. *Infect Immun* 78, 552-561.

O'Hara, J. M., Whaley, K., Pauly, M., Zeitlin, L. and Mantis, N. J. (2012) Plantbased expression of a partially humanized neutralizing monoclonal IgG directed against an immunodominant epitope on the ricin toxin A subunit. *Vaccine* 30, 1239-1243.

Ohme-Takagi, M., Taylor, C., Newman, T. and Green, P. (1993) The effect of sequences with high AU content on mRNA stability in tobacco. *Proc Natl Acad Sci USA* 90, 11811-11815.

Olea-Popelka, F., McLean, M. D., Horsman, J., Almquist, K., Brandle, J. E. and Hall, J. C. (2005) Increasing expression of an anti-picloram single-chain variable fragment (ScFv) antibody and resistance to picloram in transgenic tobacco (*Nicotiana tabacum*). *J Agric Food Chem* 53, 6683-6690.

Padlan, E. A. (1994) Anatomy of the antibody molecule. *Molecular immunology* 31, 169-217.

Rothnie, H. M. (1996) Plant mRNA 3'-end formation. *Plant Mol Biol* 32, 43-61.

Roque, A. C., Silva, C. S. and Taipa, M. Â. (2007) Affinity-based methodologies and ligands for antibody purification: Advances and perspectives. *Journal of Chromatography A* 1160, 44-55.

Samac, D. A., Hironaka, C. M., Yallaly, P. E. and Shah, D. M. (1990) Isolation and Characterization of the Genes Encoding Basic and Acidic Chitinase in *Arabidopsis thaliana. Plant Physiol* 93, 907-914.

Saunders, J. A., Matthews, B. F. and Romeo, J. (2001) Regulation of phytochemicals by molecular techniques. Vol. 35. Elsevier.

Shahmuradov, I. A., Gammerman, A. J., Hancock, J. M., Bramley, P. M. and Solovyev, V. V. (2003) PlantProm: a database of plant promoter sequences. *Nucleic Acids Research* 31, 114-117.

Shapiro, M. B. and Senapathy, P. (1987) RNA splice junctions of different classes of eukaryotes: sequence statistics and functional implications in gene expression. *Nucleic Acids Res* 5, 7155-7174.

Smallshaw, J. E. and Vitetta, E. S. (2011) Ricin vaccine development. *Ricin and Shiga Toxins*. Springer Berlin Heidelberg, 259-272.

Stöger, E., Sack, M., Nicholson, L., Fischer, R. and Christou, P. (2005) Recent progress in plantibody technology. *Curr Pharm Des* 11, 2439-2457.

Strasser, R., Stadlmann, J., Schähs, M., Stiegler, G., Quendler, H., Mach, L., Glössl, J., Weterings, K., Pabst, M. and Steinkellner, H. (2008) Generation of glyco-engineered *Nicotiana benthamiana* for the production of monoclonal antibodies with a homogeneous human-like N-glycan structure. *Plant Biotechnol J* 6, 392-402.

Vézina, L., Faye, L., Lerouge, P., D'Aoust, M., Marquet-Blouin, E., Burel, C., Lavoie, P., Bardor, M., and Gomord, V. (2009) Transient co-expression for fast and high-yield production of antibodies with human-like N-glycans in plants. *Plant Biotechnol J* 7, 442-455.

Weintraub, J. A., Hilton, J. F., White, J. M., Hoover, C. I., Wycoff, K. L., Yu, L., Larrick, J. W. and Featherstone, J. D. (2005) Clinical trial of a plant-derived antibody on recolonization of mutans streptococci. *Caries Res* 39, 241-250.

Yu, D., McLean, M. D., Hall, J. C. and Ghosh, R. (2008) Purification of a human immunoglobulin G1 monoclonal antibody from transgenic tobacco using membrane chromatographic processes. *J Chromatogr A* 1187, 128-137.

The invention claimed is:

1. A method of making an antibody or antibody fragment in a plant that binds to ricin B chain comprising:
   (a) introducing a nucleic acid molecule encoding a heavy chain variable region of the antibody and a nucleic acid molecule encoding a light chain variable region of the antibody into a plant or plant cell;
   (b) introducing a nucleic acid molecule encoding a P19 suppressor of gene-silencing protein into the plant or plant cell; and
   (c) growing the plant or plant cell to obtain a plant that expresses the antibody or antibody fragment,
   wherein the nucleic acid molecule encoding the heavy chain variable region and the nucleic acid molecule encoding the light chain variable region of the antibody are introduced on the same T-DNA vector, the T-DNA vector comprising a left border and a right border,
   wherein the nucleic acid molecule encoding the heavy chain variable region and the nucleic acid molecule encoding the light chain variable region are in opposite and divergent transcriptional orientations,
   wherein the nucleic acid molecule encoding the heavy chain variable region is between the left border and the nucleic acid molecule encoding the light chain variable region,
   wherein the nucleic acid molecule encoding the light chain variable region is between the nucleic acid molecule encoding the heavy chain variable region and the right border,
   wherein the nucleic acid molecule encoding the P19 suppressor of gene-silencing protein is introduced on a separate vector from the T-DNA vector comprising the nucleic acid molecule encoding the heavy chain variable region and the nucleic acid molecule encoding the light chain variable region of the antibody, and
   wherein the nucleic acid molecule encoding the heavy chain variable region comprises the Complementarity Determining Region (CDR) H1 sequence as shown in SEQ ID NO: 2, the CDR H2 sequence as shown in SEQ ID NO: 3, and the CDR H3 sequence as shown in SEQ ID NO: 4 or the heavy chain variable region comprises the amino acid sequence of CDR H1 as shown in SEQ ID NO: 6, the amino acid sequence of CDR H2 as shown in SEQ ID NO: 7, and the amino acid sequence of CDR H3 as shown in SEQ ID NO: 8 and
   wherein the nucleic acid molecule encoding the light chain variable region comprises the CDR Li sequence as shown in SEQ ID NO: 10, the CDR L2 sequence as shown in SEQ ID NO: 11, and the CDR L3 sequence as shown in SEQ ID NO: 12 or the light chain variable region comprises the amino acid sequence of CDR L1 as shown in SEQ ID NO: 14, the amino acid sequence of CDR L2 as shown in SEQ ID NO: 15, and the amino acid sequence of CDR L3 as shown in SEQ ID NO: 16.

2. The method according to claim 1, further comprising introducing a nucleic acid molecule encoding human 1,4-galactosyltransferase (GalT) into the plant or plant cell.

3. The method according to claim 1, wherein the nucleic acid molecule encoding the heavy chain variable region comprises a sequence as shown in SEQ ID NO:1, or a sequence at least 75% identical to SEQ ID NO:1 or the framework region thereof and/or the heavy chain variable region comprises the amino acid sequence as shown in SEQ ID NO:5, or a sequence at least 75% identical to SEQ ID NO:5 or the framework region thereof.

4. The method according to claim 1, wherein the nucleic acid molecule encoding the light chain variable region comprises a sequence as shown in SEQ ID NO:9, or a sequence at least 75% identical to SEQ ID NO:9 or to the framework region thereof and/or wherein the light chain variable region comprises the amino acid sequence as shown in SEQ ID NO:13, or a sequence at least 75% identical to SEQ ID NO:13 or the framework region thereof.

5. The method according to claim 1, wherein the plant is N. benthamiana.

6. The method according to claim 1, wherein the antibody or antibody fragment is purified and polished by contacting the antibody or antibody fragment with Butyl HP resin.

7. The method of claim 1, wherein the nucleic acid molecule encoding the P19 suppressor of gene-silencing protein comprises the amino acid sequence shown in SEQ ID NO: 18, or a sequence at least 95% identical thereof.

* * * * *

SEQUENCE LISTING

```
<160> NUMBER OF SEQ ID NOS: 21

<210> SEQ ID NO 1
<211> LENGTH: 348
<212> TYPE: DNA
<213> ORGANISM: Artificial Sequence
<220> FEATURE:
<223> OTHER INFORMATION: Synthetic construct

<400> SEQUENCE: 1
caagtccagt tggttcaaag cggagctgaa gttaagaaac ctggagcttc tgtaaaagtg      60
tcttgtaaag ctagtggata tacttttact gaacacatca ttaattgggt gaggcaagct     120
ccaggtcaaa acttggaatg gatgggactt attaatccta atagcggagg cactaactac     180
aaccaaaagt tcaaggatcg tgtgactatg actaccgata cttctacttc cactgcctat     240
atggagttgc tcagccttcg ttccgatgac acagcagttt attactgtgc aaggttgaga     300
tatgatgctg cctactgggg tcaggggaca actgttactg ttagttct                  348

<210> SEQ ID NO 2
<211> LENGTH: 15
<212> TYPE: DNA
<213> ORGANISM: Artificial Sequence
<220> FEATURE:
<223> OTHER INFORMATION: Synthetic construct

<400> SEQUENCE: 2
gaacacatca ttaat                                                       15

<210> SEQ ID NO 3
<211> LENGTH: 51
<212> TYPE: DNA
<213> ORGANISM: Artificial Sequence
<220> FEATURE:
<223> OTHER INFORMATION: Synthetic construct

<400> SEQUENCE: 3
cttattaatc ctaatagcgg aggcactaac tacaaccaaa agttcaagga t                51

<210> SEQ ID NO 4
<211> LENGTH: 21
<212> TYPE: DNA
<213> ORGANISM: Artificial Sequence
<220> FEATURE:
<223> OTHER INFORMATION: Synthetic construct

<400> SEQUENCE: 4
ttgagatatg atgctgccta c                                                21
```

<210> SEQ ID NO 5
<211> LENGTH: 116
<212> TYPE: PRT
<213> ORGANISM: Artificial Sequence
<220> FEATURE:
<223> OTHER INFORMATION: Synthetic construct

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu His
            20                  25                  30

Ile Ile Asn Trp Val Arg Gln Ala Pro Gly Gln Asn Leu Glu Trp Met
        35                  40                  45

Gly Leu Ile Asn Pro Asn Ser Gly Gly Thr Asn Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Leu Ser Leu Arg Ser Asp Asp Thr Ala Val Tyr Tyr Cys
                85                  90                  95

Ala Arg Leu Arg Tyr Asp Ala Ala Tyr Trp Gly Gln Gly Thr Thr Val
            100                 105                 110

Thr Val Ser Ser
        115

<210> SEQ ID NO 6
<211> LENGTH: 5
<212> TYPE: PRT
<213> ORGANISM: Artificial Sequence
<220> FEATURE:
<223> OTHER INFORMATION: Synthetic construct

<400> SEQUENCE: 6

Glu His Ile Ile Asn
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic construct

<400> SEQUENCE: 7

Leu Ile Asn Pro Asn Ser Gly Gly Thr Asn Tyr Asn Gln Lys Phe Lys
1               5                   10                  15

Asp

<210> SEQ ID NO 8
<211> LENGTH: 7
<212> TYPE: PRT
<213> ORGANISM: Artificial Sequence
<220> FEATURE:
<223> OTHER INFORMATION: Synthetic construct

<400> SEQUENCE: 8

Leu Arg Tyr Asp Ala Ala Tyr
1               5

<210> SEQ ID NO 9
<211> LENGTH: 321

<212> TYPE: DNA
<213> ORGANISM: Artificial Sequence
<220> FEATURE:
<223> OTHER INFORMATION: Synthetic construct

<400> SEQUENCE: 9

```
gatatccaaa tgactcagtc accatcatct ttgagtgctt cagtgggtga ccgtgtcacc      60
attacatgta aggccagcca ggatgtgaca gccgctgtcg cctggtatca gcaaaagcca     120
ggaaaagcac ctaaattgct tatttactct gctagctaca ggtatacagg tgttcctagt     180
agatttagtg gatcaggatc tgggactgat ttcacactga caataagctc tcttcaacca     240
gaagatttcg caacttatta ctgccaacag tactataaca ctccattgac ttttgggggt     300
ggcactaagg ttgagatcaa g                                               321
```

<210> SEQ ID NO 10
<211> LENGTH: 33
<212> TYPE: DNA
<213> ORGANISM: Artificial Sequence
<220> FEATURE:
<223> OTHER INFORMATION: Synthetic construct

<400> SEQUENCE: 10

```
aaggccagcc aggatgtgac agccgctgtc gcc                                   33
```

<210> SEQ ID NO 11
<211> LENGTH: 21
<212> TYPE: DNA
<213> ORGANISM: Artificial Sequence
<220> FEATURE:
<223> OTHER INFORMATION: Synthetic construct

<400> SEQUENCE: 11

```
tctgctagct acaggtatac a                                                21
```

<210> SEQ ID NO 12
<211> LENGTH: 27
<212> TYPE: DNA
<213> ORGANISM: Artificial Sequence
<220> FEATURE:
<223> OTHER INFORMATION: Sythetic construct

<400> SEQUENCE: 12

```
caacagtact ataacactcc attgact                                          27
```

<210> SEQ ID NO 13
<211> LENGTH: 107
<212> TYPE: PRT
<213> ORGANISM: Artificial Sequence
<220> FEATURE:
<223> OTHER INFORMATION: Synthetic construct

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Ala Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Tyr Asn Thr Pro Leu
                85                  90                  95

Thr Phe Gly Gly Gly Thr Lys Val Glu Ile Lys
            100                 105

<210> SEQ ID NO 14
<211> LENGTH: 11
<212> TYPE: PRT
<213> ORGANISM: Artificial Sequence
<220> FEATURE:
<223> OTHER INFORMATION: Synthetic construct

<400> SEQUENCE: 14

Lys Ala Ser Gln Asp Val Thr Ala Ala Val Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic construct

<400> SEQUENCE: 15

Ser Ala Ser Tyr Arg Tyr Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic construct

<400> SEQUENCE: 16

Gln Gln Tyr Tyr Asn Thr Pro Leu Thr
1               5

<210> SEQ ID NO 17
<211> LENGTH: 516
<212> TYPE: DNA
<213> ORGANISM: Tomato bushy stunt virus

<400> SEQUENCE: 17
atggaaaggg ctattcaggg aaatgatgct agagagcagg ctaattctga agatgggat      60 ggtggatctg gtggaactac ttctccattc aagcttccag atgagtctcc atcttggact    120
gagtggaggc ttcataacga tgagactaac tccaatcagg ataacccact cggattcaaa    180
gaatctgggg gattcggaaa ggttgtgttc aagcgttacc ttaggtatga taggactgag    240
gcttcacttc atagggttct cggatcttgg actggtgatt ctgttaacta cgctgcttct    300 cgttttttg gattcgatca gatcggatgc acttactcta ttaggttcag gggagtgtct    360
attactgttt ctggtggatc taggactctt caacaccttt gcgagatggc tattaggtct    420
aagcaagagc ttcttcagct tgctccaatt gaggttgagt ctaacgtttc aagaggatgt    480
ccagaaggta ctgagacttt cgagaaagaa tccgag                              516

<210> SEQ ID NO 18
<211> LENGTH: 172
<212> TYPE: PRT
<213> ORGANISM: Tomato bushy stunt virus

<400> SEQUENCE: 18

```
Met Glu Arg Ala Ile Gln Gly Asn Asp Ala Arg Glu Gln Ala Asn Ser
1               5                   10                  15

Glu Arg Trp Asp Gly Gly Ser Gly Gly Thr Thr Ser Pro Phe Lys Leu
            20                  25                  30

Pro Asp Glu Ser Pro Ser Trp Thr Glu Trp Arg Leu His Asn Asp Glu
                35                  40                  45

Thr Asn Ser Asn Gln Asp Asn Pro Leu Gly Phe Lys Glu Ser Trp Gly
        50                  55                  60

Phe Gly Lys Val Val Phe Lys Arg Tyr Leu Arg Tyr Asp Arg Thr Glu
65                  70                  75                  80

Ala Ser Leu His Arg Val Leu Gly Ser Trp Thr Gly Asp Ser Val Asn
                85                  90                  95

Tyr Ala Ala Ser Arg Phe Phe Gly Phe Asp Gln Ile Gly Cys Thr Tyr
                100                 105                 110

Ser Ile Arg Phe Arg Gly Val Ser Ile Thr Val Ser Gly Gly Ser Arg
            115                 120                 125

Thr Leu Gln His Leu Cys Glu Met Ala Ile Arg Ser Lys Gln Glu Leu
        130                 135                 140

Leu Gln Leu Ala Pro Ile Glu Val Glu Ser Asn Val Ser Arg Gly Cys
145                 150                 155                 160

Pro Glu Gly Thr Glu Thr Phe Glu Lys Glu Ser Glu
                165                 170
```

<210> SEQ ID NO 19
<211> LENGTH: 1149
<212> TYPE: DNA
<213> ORGANISM: Homo sapiens

<400> SEQUENCE: 19

```
atgattcaca cgaacctgaa gaagaagttc agcctcttca tcctggtttt cctgctcttc      60
gcggtaatct gcgtttggaa gaagggttct gactacgaag ccctcaccct ccaggcgaag     120
gaattccaga tgccgaagtc tcaggagaag gttgccgcag ccatcggtca gtcctctggt     180
gaactccgta ccggtggtgc tcgtcctcca ccgccgctgg gtgcatctag ccagccgcgt     240
ccgggtggcg acagctctcc ggttgtggat tctggcccag gtccagcttc taacctgacg     300
tctgttccgg ttccacatac caccgcgctc agcctgccgg cgtgcccgga agaatctccg     360
ctgctggtag gccctatgct catcgaattc aacatgccgg tagacctgga actcgttgcg     420
aagcagaacc cgaacgtaaa gatgggtggt cgctacgccc tcgtgattg cgtttccccg     480
cacaaggtgg ccatcatcat tcctttccgt aaccgtcaag agcacctgaa atactggctg     540
tactacctgc acccggttct gcagcgtcag cagctcgact acggtatcta cgttatcaac     600
caggcgggtg acaccatctt taaccgcgct aaactgctga acgtgggttt ccaggaggcg     660
ctcaaggatt acgactacac ctgcttcgtt ttctctgacg ttgacctgat cccgatgaat     720
gatcacaacg cctaccgttg cttttctcaa ccacgtcaca tctctgttgc gatggacaaa     780
ttcggttcct ctctcccgta tgtacagtac ttcggtggcg tgtctgccct ctctaagcag     840
caattcctga cgatcaacgg tttcccgaac aattactggg gttggggtgg tgaagacgat     900
gatatcttca accgcctcgt attccgcggt atgtctatca gccgtccgaa tgcggtcgtg     960
ggccgctgcc gtatgatccg tcacagccgg acaagaaga cgagccgaa cccgcagcgc    1020
tttgaccgta tcgcgcacac caaagaaact atgctgtctg acggcctgaa ctctctcacg    1080
taccaagttc tcgacgtaca gcgttacccg ctgtatacc agatcaccgt cgacatcggt    1140
``` accccgtct 1149

<210> SEQ ID NO 20
<211> LENGTH: 383
<212> TYPE: PRT
<213> ORGANISM: Homo sapiens

<400> SEQUENCE: 20

Met Ile His Thr Asn Leu Lys Lys Phe Ser Leu Phe Ile Leu Val
1               5                   10                  15

Phe Leu Leu Phe Ala Val Ile Cys Val Trp Lys Lys Gly Ser Asp Tyr
                20                  25                  30

Glu Ala Leu Thr Leu Gln Ala Lys Glu Phe Gln Met Pro Lys Ser Gln
            35                  40                  45

Glu Lys Val Ala Ala Ile Gly Gln Ser Ser Gly Glu Leu Arg Thr
    50                  55                  60

Gly Gly Ala Arg Pro Pro Pro Leu Gly Ala Ser Ser Gln Pro Arg
65                  70                  75                  80

Pro Gly Gly Asp Ser Ser Pro Val Val Asp Ser Gly Pro Gly Pro Ala
                85                  90                  95

Ser Asn Leu Thr Ser Val Pro Val Pro His Thr Ala Leu Ser Leu
                100                 105                 110

Pro Ala Cys Pro Glu Glu Ser Pro Leu Leu Val Gly Pro Met Leu Ile
        115                 120                 125

Glu Phe Asn Met Pro Val Asp Leu Glu Leu Val Ala Lys Gln Asn Pro
    130                 135                 140

Asn Val Lys Met Gly Gly Arg Tyr Ala Pro Arg Asp Cys Val Ser Pro
145                 150                 155                 160

His Lys Val Ala Ile Ile Pro Phe Arg Asn Arg Gln Glu His Leu
                165                 170                 175

Lys Tyr Trp Leu Tyr Tyr Leu His Pro Val Leu Gln Arg Gln Gln Leu
                180                 185                 190

Asp Tyr Gly Ile Tyr Val Ile Asn Gln Ala Gly Asp Thr Ile Phe Asn
    195                 200                 205

Arg Ala Lys Leu Leu Asn Val Gly Phe Gln Glu Ala Leu Lys Asp Tyr
    210                 215                 220

Asp Tyr Thr Cys Phe Val Phe Ser Asp Val Asp Leu Ile Pro Met Asn
225                 230                 235                 240

Asp His Asn Ala Tyr Arg Cys Phe Ser Gln Pro Arg His Ile Ser Val
                245                 250                 255

Ala Met Asp Lys Phe Gly Phe Ser Leu Pro Tyr Val Gln Tyr Phe Gly
            260                 265                 270

Gly Val Ser Ala Leu Ser Lys Gln Gln Phe Leu Thr Ile Asn Gly Phe
        275                 280                 285

Pro Asn Asn Tyr Trp Gly Trp Gly Gly Glu Asp Asp Ile Phe Asn
    290                 295                 300

Arg Leu Val Phe Arg Gly Met Ser Ile Ser Arg Pro Asn Ala Val Val
305                 310                 315                 320

Gly Arg Cys Arg Met Ile Arg His Ser Arg Asp Lys Lys Asn Glu Pro
                325                 330                 335

Asn Pro Gln Arg Phe Asp Arg Ile Ala His Thr Lys Glu Thr Met Leu
                340                 345                 350

Ser Asp Gly Leu Asn Ser Leu Thr Tyr Gln Val Leu Asp Val Gln Arg
            355                 360                 365

```
Tyr Pro Leu Tyr Thr Gln Ile Thr Val Asp Ile Gly Thr Pro Ser
    370                 375                 380

<210> SEQ ID NO 21
<211> LENGTH: 21
<212> TYPE: PRT
<213> ORGANISM: Arabidopsis thaliana

<400> SEQUENCE: 21

Met Ala Lys Thr Asn Leu Phe Leu Phe Leu Ile Phe Ser Leu Leu Leu
1               5                   10                  15

Ser Leu Ser Ser Ala
            20
```